United States Patent
Cooper et al.

(10) Patent No.: US 10,571,463 B2
(45) Date of Patent: Feb. 25, 2020

(54) BIOMARKER PANEL FOR DOSE ASSESSMENT OF RADIATION INJURY AND MICRO PLASMA FILTER

(71) Applicant: SRI INTERNATIONAL, Menlo Park, CA (US)

(72) Inventors: David E. Cooper, Menlo Park, CA (US); Robert Balog, Menlo Park, CA (US); Polly Chang, Menlo Park, CA (US); Thomas A. Shaler, Menlo Park, CA (US); Hua Lin, Menlo Park, CA (US); Annalisa D'Andrea, Menlo Park, CA (US); Travis Harrison, Menlo Park, CA (US); Roger H. Schmidt, Menlo Park, CA (US); Christina Swanson, Menlo Park, CA (US); Estevan Mendoza, Menlo Park, CA (US); Mark Steele, Menlo Park, CA (US); Pablo E. Garcia, Menlo Park, CA (US)

(73) Assignee: SRI INTERNATIONAL, Menlo Park, CA (US)

(*) Notice: Subject to any disclaimer, the term of this patent is extended or adjusted under 35 U.S.C. 154(b) by 0 days.

(21) Appl. No.: 16/042,108

(22) Filed: Jul. 23, 2018

(65) Prior Publication Data
US 2018/0321228 A1 Nov. 8, 2018

Related U.S. Application Data

(63) Continuation of application No. 14/964,579, filed as application No. PCT/US2014/046058 on Jul. 9, 2014, now abandoned.

(60) Provisional application No. 61/844,365, filed on Jul. 9, 2013.

(51) Int. Cl.
*G01N 33/53* (2006.01)
*G01N 33/68* (2006.01)
*G01N 33/49* (2006.01)
*G01N 33/558* (2006.01)

(52) U.S. Cl.
CPC ....... *G01N 33/5302* (2013.01); *G01N 33/491* (2013.01); *G01N 33/558* (2013.01); *G01N 33/6893* (2013.01); *G01N 2800/40* (2013.01)

(58) Field of Classification Search
None
See application file for complete search history.

(56) References Cited

U.S. PATENT DOCUMENTS

| 4,668,399 A | 5/1987 | Duggins |
| 4,729,829 A | 3/1988 | Duggins |
| 5,283,038 A | 2/1994 | Seymour |
| 2009/0197280 A1 | 8/2009 | Bangert et al. |
| 2009/0269744 A1* | 10/2009 | Krause ............ C12Q 1/6886 435/6.14 |
| 2010/0055721 A1 | 3/2010 | Lambert et al. |
| 2012/0329070 A1 | 12/2012 | Blakely et al. |
| 2013/0052668 A1 | 2/2013 | Paulovich et al. |
| 2014/0228233 A1 | 8/2014 | Pawlowski et al. |
| 2015/0151035 A1 | 6/2015 | Huemer |
| 2016/0109437 A1 | 4/2016 | Cooper et al. |

FOREIGN PATENT DOCUMENTS

| EP | 0112173 B1 | 8/1989 |
| JP | S5912016 A | 1/1984 |
| WO | WO-2013/049455 A1 | 4/2013 |
| WO | WO-2015/006515 A1 | 1/2015 |

OTHER PUBLICATIONS

Oh et al. (J. Proteome Res ; 2011 10: 1406-1415) (Year: 2011).*
Nguyen et al. (Scand. J. Rheumatol. 2011 40:197-204) (Year: 2011).*
Akashi, M., et al. (2001), Initial symptoms of acute radiation syndrome in the JCO criticality accident in Tokai-mura, J Radiat Res, 42 Suppl, S157-166.
Barrett, A., A. Jacobs, J. Kohn, J. Raymond, and R. L. Fowles (1982), Changes in serum amylase and its isoenzymes after whole body irradiation, Br Med J (Clin Res Ed), 285(6336), 170-171.
Bertho, J. M., and L. Roy (2009), A rapid multiparametric method for victim triage in cases of accidental protracted irradiation or delayed analysis, Br J Radiol, 82(981), 764-770.
Bertho, J. M., et al. (2001), Level of Flt3-ligand in plasma: a possible new bio-indicator for radiation-induced aplasia, Int J Radiat Biol, 77(6), 703-712.
Blakely, W. F., et al. (2011), Murine partial-body radiation exposure model for biodosimetry studies—preliminary report, Radiation measurements, 46, 898-902.
Blakely, W. F.,et al.(2010), Multiple parameter radiation injury assessment using a nonhuman primate radiation model-biodosimetry applications, Health Phys, 98(2), 153-159.
Brattstrom, C., et al. (1991), Isoamylase levels in bone marrow transplant patients are affected by total body irradiation and not by graft-versus-host disease, Transpl Int, 4(2), 96-98.
Cao, S., et al. (1998a), Interleukin 15 protects against toxicity and potentiates antitumor activity of 5-fluorouracil alone and in combination with leucovorin in rats bearing colorectal cancer, Cancer Res, 58(8), 1695-1699.
Cao, S., et al. (1998b), Interleukin 15 offers selective protection from irinotecan-induced intestinal toxicity in a preclinical animal model, Cancer Res, 58(15), 3270-3274.
Christensson, A., et al. (1993), Serum prostate specific antigen complexed to alpha 1-antichymotrypsin as an indicator of prostate cancer, J Urol, 150(1), 100-105.

(Continued)

*Primary Examiner* — Changhwa J Cheu
(74) *Attorney, Agent, or Firm* — Ballard Spahr LLP (57) ABSTRACT

Materials, systems and methods are provided for qualitative assessment of exposure of a person to ionizing radiation by measuring amounts of the biomarkers, wherein a change compared with corresponding un-irradiated control reference ranges of the biomarkers, provides the assessment, wherein the biomarkers include (i) alpha-1-Antichymotrypsin (ACT), (ii) Fms-related tyrosine kinase 3 ligand (Flt3L), and (iii) one or more additional proteins.

11 Claims, 1 Drawing Sheet

(56) References Cited

OTHER PUBLICATIONS

Cowland, J. B., and N. Borregaard (1997), Molecular characterization and pattern of tissue expression of the gene for neutrophil gelatinase-associated lipocalin from humans, Genomics, 45(1), 17-23.
Dubray, B., et al. (1992), Post-irradiation hyperamylasemia as a biological dosimeter, Radiother Oncol, 24(1), 21-26.
Guipaud, O., et al. (2009), Protein biomarkers for radiation exposure: towards a proteomic approach as a new investigation tool, Ann 1st Super Sanita, 45(3), 278-286.
Hong, J. H., et al. (1995), Induction of acute phase gene expression by brain irradiation, Int J Radiat Oncol Biol Phys, 33(3), 619-626.
Junglee, D., A. Katrak, J. Mohiuddin, H. Blacklock, H. G. Prentice, and P. Dandona (1986), Salivary amylase and pancreatic enzymes in serum after total body irradiation, Clin Chem, 32(4), 609-610.
Lai, Y. G., et al. (1999), IL-15 promotes survival but not effector function differentiation of CD8+ TCRalphabeta+ intestinal intraepithelial lymphocytes, JImmunol, 163(11), 5843-5850.
Lilja, H., et al. (1991), Prostate-specific antigen in serum occurs predominantly in complex with alpha 1-antichymotrypsin, Clin Chem, 37(9), 1618-1625.
Lugering, N., et al. (1999), Interleukin-15 strongly inhibits interleukin-8 and monocyte chemoattractant protein-1 production in human colonic epithelial cells, Immunology, 98(4), 504-509.
Mal'tsev, V. N., et al. (2006), [The individual prognosis of the gravity and of the outcome of acute radiation disease based on immunological indexes], Radiatsionnaia biologiia, radioecologiia / Rossiiskaia akademiia nauk, 46(2), 152-158.
Noto, A., et al. (2013), NGAL and Metabolomics: The Single Biomarker to Reveal the Metabolome Alterations in Kidney Injury, Biomed Res Int, 2013, 612032.
Ossetrova, N. I., et al. (2007), The use of discriminant analysis for evaluation of early-response multiple biomarkers of radiation exposure using non-human primate 6-Gy whole-body radiation model, Radiation Measurements, 42, 1158-1163.
Ossetrova, N. I., et al. (2009), Multiple blood-proteins approach for early-response exposure assessment using an in vivo murine radiation model, Int J Radiat Biol, 85(10), 837-850.
Ossetrova, N. I., et al. (2010), Combined approach of hematological biomarkers and plasma protein SAA for improvement of radiation dose assessment triage in biodosimetry applications, Health Phys, 98(2), 204-208.
Ossetrova, N., et al. (2011), C-reactive protein and serum amyloid A as early phase and prognostic indicators of acute radiation exposure in nonhuman primate total-body irradiation, Radiation measurements, 46, 1019-1024.
Patel, et al. "Ionizing radiation and TNF-alpha and stimulated expression of alpha 1-antichymotrypsin gene in human squamous carcinoma cells," Acta Oncol. 1998, vol. 37, pp. 475-478 (Abstract).
Prat, M., et al. (2005), Radiation-induced increase in plasma Flt3 ligand concentration in mice: evidence for the implication of several cell types, Radiat Res, 163(4), 408-417.
Prat M et al.(2006), Use of flt3 ligand to evaluate residual hematopoiesis after heterogeneous irradiation in mice, Radiat Res, 166(3), 504-511.

Reinecker, H. C., et al. (1996), Intestinal epithelial cells both express and respond to interleukin 15, Gastroenterology, 111(6), 1706-1713.
Roudkenar, M. H., et al. (2007), Oxidative stress induced lipocalin 2 gene expression: addressing its expression under the harmful conditions, J Radiat Res, 48(1), 39-44.
Sharma, M., et al. (2013), The urine proteome as a radiation biodosimeter, Adv Exp Med Biol, 990, 87-100.
Shiiba, M., et al. (2013), Lipocalin-2 is associated with radioresistance in oral cancer and lung cancer cells, Int J Oncol, 42(4), 1197-1204.
Sugihara, T., et al. (2013), In vivo partial bystander study in a mouse model by chronic medium-dose-rate gamma-ray irradiation, Radiat Res, 179(2), 221-231.
Thermo Scientific, "Thermo Scientific Finnpipette Finntip: Product Catalog 2010," 2009, pp. 1-40. Retrieved from the Internet: <www.tslabor.hu/depo/Finnpipette_Finntip_2010_Catalog.pdf>.
Van der Velden, W. J., et al. (2010), Intestinal damage determines the inflammatory response and early complications in patients receiving conditioning for a stem cell transplantation, PLoS One, 5(12), e15156.
Ward, et al. "Conventional apheresis therapies: a review," J Clin Apher. (2011), vol. 26, pp. 230-238.
Zhang, Y., et al. (2009), Synergistic protecting effect of cord blood CD34+ cells over-expressing both interleukin-3 and Flt3 ligand on lethally irradiated mice, Int J Hematol, 90(1), 64-73.
International Search Report and Written Opinion dated Nov. 21, 2014 by the International Searching Authority for International Application No. PCT/US2014/046058, filed on Jul. 9, 2014 and published as WO 2015/006515 on Jan. 15, 2015 (Applicant-SRI International) (11 Pages).
International Preliminary Report on Patentability dated Jan. 12, 2016 by the International Searching Authority for International Application No. PCT/US2014/046058, filed on Jul. 9, 2014 and published as WO 2015/006515 on Jan. 15, 2015 (Applicant—SRI International) (10 Pages).
Notification of Reasons for Refusal dated Jul. 17, 2018 by the Japanese Patent Office for JP Application No. 2016-525470, filed on Jul. 9, 2014 and published as JP 2016533497A on Oct. 27, 2016 (Applicant—SRI International) (Translation—3 pages).
Requirement for Restriction/Election dated Aug. 9, 2017 by the USPTO for U.S. Appl. No. 14/964,579, filed Dec. 10, 2015 and published as US 2016-0109437 A1 on Apr. 21, 2016 (Inventor—David E. Cooper et al.) ( pages).
Response to Requirement for Restriction/Election dated Sep. 8, 2017 to the USPTO for U.S. Appl. No. 14/964,579, filed Dec. 10, 2015 and published as US 2016-0109437 A1 on Apr. 21, 2016 (Inventor—David E. Cooper et al.) (5 pages).
Non Final Rejection dated Jan. 24, 2018 by the USPTO for U.S. Appl. No. 14/964,579, filed Dec. 10, 2015 and published as US 2016-0109437 A1 on Apr. 21, 2016 (Inventor—David E. Cooper et al.) (16 pages).
Notice of Abandonment dated Oct. 16, 2018 by the USPTO for U.S. Appl. No. 14/964,579, filed Dec. 10, 2015 and published as US 2016-0109437 A1 on Apr. 21, 2016 (Inventor—David E. Cooper et al.) (2 pages).

* cited by examiner

BIOMARKER PANEL FOR DOSE ASSESSMENT OF RADIATION INJURY AND MICRO PLASMA FILTER

CROSS-REFERENCE TO RELATED APPLICATION

This application is a continuation of PCT/US14/46058; filed Jul. 9, 2014, which claims priority to Ser. No. 61/844,365, filed: Jul. 9, 2013, the disclosures of which is incorporated herein by reference in their entirety.

This invention was made with government support under Department of Health and Human Services contract no. HHSO100201000007C. The government has certain rights in the invention.

INTRODUCTION

We have developed and disclose a point-of-care (POC) radiation dose-assessment tool for rapid triage of individuals who may have been exposed to ionizing radiation (IR) during a radiological/nuclear event. Our approach combines a mature handheld detection technology platform based on upconverting phosphor-reporter technology (UPT) with a simple, sensitive, fast (<15 min) assay format and a biomarker panel for the rapid development of a biodosimeter tool that meets BARDA requirements. We demonstrate use of multiple proteomic targets to provide enhanced accuracy in predicting early-phase radiation exposure. The system detects biomarkers in a noninvasively collected blood sample that can provide qualitative and quantitative measures of an individual's exposure to IR.

Guipaud et al suggested a panel that includes amylase, Flt3-Ligand and citrulline in the murine model [Guipaud and Benderitter, 2009] while GADD45 (Growth arrest and DNA damage inducible gene 45), interleukin 6 (IL-6) and salivary alpha amylase (AMY1A) are included in the murine panel described by Ossetrova et al [N. I. Ossetrova and Blakely, 2009]. Other ration responsive proteins have been reported: serum Amylase A [Blakely et al., 2010; N Ossetrova et al., 2011; N. I. Ossetrova and Blakely, 2009; N. I. Ossetrova et al., 2010; N. I. Ossetrova et al., 2007; Barrett et al., 1982; Junglee et al., 1986; Junglee et al., 1986; Dubray et al., 1992; Brattstrom et al., 1991; Akashi et al., 2001]; Fms-related tyrosine kinase 3 ligand (Flt3L) [Zhang et al., 2009; Prat et al., 2005; Prat et al., 2006; Blakely et al., 2011; Bertho et al., 2001; Bertho and Roy, 2009]; Lipocalin-2 (LCN2), [Cowland and Borregaard, 1997; Noto et al., 2013; Roudkenar et al., 2007; Shiiba et al., 2013; Sugihara et al., 2013]; Alpha 1-antichymotrypsin (ACT) [Christensson et al., 1993; Lilja et al., 1991; Hong et al., 1995; Patel et al., 1998; Sharma and Moulder, 2013]; Interleukin 15 (IL15) [Lai et al., 1999; Lugering et al., 1999; Reinecker et al., 1996; Cao et al., 1998a; Cao et al., 1998b].

SUMMARY OF THE INVENTION

The invention provides materials, systems and methods for qualitative assessment of exposure of a person to ionizing radiation by measuring amounts of the biomarkers, wherein a change, which may be a significant increase or decrease or a pattern of relative differences in the amounts, compared with corresponding un-irradiated control reference ranges of the biomarkers, provides the assessment.

The biomarkers comprise, or consist of, or consist essentially of (the latter meaning that the assessment derives from the recited biomarkers, though others may be incidentally present) (i) alpha-1-Antichymotrypsin (ACT), (ii) Fms-related tyrosine kinase 3 ligand (Flt3L), and (iii) one, two, three or more additional proteins selected from the group consisting of:

| | |
|---|---|
| Serum amyloid A isoform 1 or 2 (SAA1 or SAA2), | Clusterin (CLU), |
| C-reactive protein (CRP), | Hemopexin (HPX), |
| Salivary alpha amylase (AMY1A), | Haptoglobin (HP), |
| Alpha-1-antitrypsin isoform 4 (SERPINA1), | Apolipoprotein A-IV (APOA4), |
| Neutrophil gelatinase-associated lipocalin (NGAL), | Interleukin 15 (IL15), |
| Alpha-1-acid glycoprotein 1 or 2, | Interleukin 18 (IL18), and |
| Leucine-rich alpha-2-glycoprotein (LRG1), | Monocyte chemotactic protein 1 (MCP1). |
| Tenascin-C (TNC), | |

Preferred additional proteins are AMY1A, NGAL, APOA4, IL15, IL18, MCP1 and HPX.

In particular embodiments, the biomarkers comprise, consist of, or consist essentially of combinations of the biomarkers, particularly preferred biomarkers and additional proteins, such as: (i) ACT, Flt3L, AMY1A and IL15; or (ii) ACT, Flt3L, NGAL and AMY1A; (iii) ACT, Flt3L, NGAL and MCP1.

In particular embodiments the methods comprises the step of separating biomarkers of a blood sample of the person, to facilitate the measuring step.

In particular embodiments, the measuring step is effected by an affinity assay, such as an lateral flow immunoassay, ELISA, microsphere-based immunoassay, Western blot, immune-dot blot, quantitative mass spectroscopy, etc.

Typically the measuring step occurs 1-7 or 1-14 days after the radiation exposure.

In particular embodiments the radiation exposure is >2Gy.

In particular embodiments the method further comprises the step of: classifying the person as either irradiation exposed or unexposed, based on the assessment, particularly above or below a predetermined exposure threshold, such 2 Gy.

In particular embodiments the method further comprises the step of treating the person for the radiation exposure, wherein the treating may be therapy, monitoring or prescribing further assessments.

The invention also provides kits adapted to the subject methods and comprising affinity capture molecules specific to the biomarkers and contained in or on a substrate, particularly wherein the substrate comprises a plurality of lateral flow strips, each having different, predetermined protein capture specificity.

In particular embodiments the kids are specifically adapted to the subject methods and comprise: (a) a capillary blood collection device, (b) a blood filter that separates plasma from blood cells, (c) a mixer that forms a mixture of the plasma and a buffer solution, (d) an applicator that applies the mixture to a lateral flow strip (or a set of strips) retained in a single cassette housing, and (e) a compact reader system that scans the lateral flow strip(s) and outputs a result reporting the amounts of the biomarkers or the assessment of exposure of a person to ionizing radiation.

In particular embodiments the reader system of the kit comprises an excitation laser, a wick selector, emission filters, collection optics, and an intensity sensor, particularly wherein the sensor comprises a photo multiplier tube, a charge-coupled device (CCD), or a complementary metal oxide semiconductor (CMOS).

The invention also provides a blood filter cartridge comprising a cylindrical housing, a chamber, an inlet, a plurality of elongate hollow apheresis fibers, each comprising a lumen and wall having pore size sufficient to pass plasma but not blood cells, and an outlet, wherein the inlet is in bulk fluid connection with the lumens, the housing confines the chamber, the fibers are contained within the chamber, and the chamber is in bulk fluid connection with the outlet, configured such that in operation, blood enters the lumens from the inlet, plasma passes though the walls of the fibers into the chamber and then out the outlet.

In embodiments the fibers are affixed at one end to a cylindrical manifold, in a grid pattern, and aligned lengthwise with the chamber, and/or the cartridge comprises 4-100 of the elongate, parallel fibers; has a dead volume of less than 100 ul; and/or requires an operating pressure of less than 2 PSI to avoid cell lysis.

The invention also provides a blood filter comprising an integrated subject cartridge, a running buffer contained in a running buffer reservoir, an actuator plunger, and a seal separating the running buffer from the cartridge inlet, configured so that depressing the plunger breaks the seal and urges the running buffer into the cartridge inlet, wherein the filter may be operably connected to a lateral flow strip, or a plurality of lateral flow strips, each optionally comprising affinity capture molecules specific to predetermined biomarkers. In particular embodiments affinity capture molecules are specific to predetermined biomarkers of exposure of a person to ionizing radiation wherein the biomarkers comprise (i) alpha-1-Antichymotrypsin (ACT), (ii) Fms-related tyrosine kinase 3 ligand (Flt3L), and (iii) one or more additional proteins selected from the group consisting of: Serum amyloid A isoform 1 or 2 (SAA1 or SAA2), C-reactive protein (CRP), Salivary alpha amylase (AMY1A), Alpha-1-antitrypsin isoform 4 (SERPINA1), Neutrophil gelatinase-associated lipocalin (NGAL), Alpha-1-acid glycoprotein 1 or 2, Leucine-rich alpha-2-glycoprotein (LRG1), Tenascin-C (TNC), Clusterin (CLU), Hemopexin (HPX), Haptoglobin (HP), Apolipoprotein A-IV (APOA4), Interleukin 15 (IL15), Interleukin 18 (IL18), and Monocyte chemotactic protein 1 (MCP1), and in embodiments, the additional proteins are selected from the group consisting of: AMY1A, NGAL, APOA4, IL15, IL18, MCP1 and HPX.

In embodiments, the biomarkers comprise: (i) ACT, Flt3L, AMY1A and IL15; or (ii) ACT, Flt3L, NGAL and AMY1A; or (iii) ACT, Flt3L, NGAL and MCP1.

The invention also provides a method of using a subject blood filter comprising the steps of: (a) separating with the filter biomarkers of a blood sample of the person; and (a) detecting the separated biomarkers.

The invention also provides a blood filter device comprising an inlet, a plurality of elongate hollow apheresis fibers, each comprising a lumen and wall having pore size, such as about 650 nm, sufficient to pass plasma but not blood cells, a chamber and an outlet, wherein the inlet is in bulk fluid connection with the lumens, the fibers are contained within the chamber, and the chamber is in bulk fluid connection with the outlet, such that in operation, blood enters the lumens from the inlet, plasma passes though the walls of the fibers into the chamber and then out the outlet.

The invention specifically provides all combinations of the recited embodiments, as if each had been laboriously individually set forth.

BRIEF DESCRIPTION OF THE DRAWINGS

FIG. 1. (a) A schematic of the hollow fiber tube separation embodiment. FIG. 1. (b) A solid works schematic of the filter assembly.

DETAILED DESCRIPTION OF PARTICULAR EMBODIMENTS AND EXAMPLES THEREOF

Blood samples were analyzed using both immunoassay and LC-MS/MS techniques to identify promising radiation responsive markers. In the NHP model we identified more than 30 plasma proteins that change in response to radiation exposure—25 of these are upregulated, and 5 are downregulated. A panel of just four of these proteins (Fms-related tyrosine kinase 3 ligand—Flt3L, Salivary alpha amylase—AMY1A, interleukin 15—IL15, and a1 antichymotrypsin—ACT) can correctly classify the NHP irradiation study samples with >96% accuracy. Replacement of IL15 with Neutrophil gelatinase-associated lipocalin (NGAL) yields essentially identical results. Other combinations of four (or more) proteins also achieve excellent classification scores, and these prove useful in distinguishing between radiation-exposed animals and animals with confounding conditions.

Three of the proteins from the NHP panel (Flt3L, IL15, and AMY1A) make an excellent classifier of the total-body-irradiated (TBI) human samples analyzed to date. These two proteins alone can classify the human data sets with an accuracy of 95% and are not confounded by either mild (or serious) infections or trauma.

We have also developed an upconverting phosphor (UPT) reporter based on lateral flow assays for four different targets of interest, and combined them into two duplex assays. The four targets investigated included Flt3L, AMY1A, C-reactive protein (CRP), and Tenascin-C (TNC). As demonstrated under previous government funding, the UPT lateral flow system is capable of achieving sensitivities comparable to an ELISA in fewer than 15 min and is therefore an ideal platform for achieving BARDA's vision of a POC radiation biodosimeter.

We also developed reader systems with UPT lateral flow assays. Sensitivities comparable to conventional immunoassays were demonstrated for Flt3L and AMY1A. A novel sample collection tool was developed that can collect a small blood volume from a finger prick, separate the plasma from the blood cells, mix the plasma with buffer, and apply a metered amount to a lateral flow device.

We developed manufacturable lateral flow assays for up to 5 different targets and a multiplex assay for 4 targets, sample collection systems integrated with the customized lateral flow cassette, and reader systems.

NHP Baseline Samples (SRI Study A246-12):

We collected baseline samples from a cohort of 28 NHPs (14 male and 14 female Rhesus Macaques that were maintained at SRI on a NIH contract (NIH-NICHD contract HHSN275200900014C). Upon approval from NIH, these animals were transferred to the BARDA biodosimetry project and enrolled into SRI study A246-12. These animals ranged in age from 11 to 16 years old (considerable older than the ~4 year old NHPs used in study M918-12 described below). The goal of this study was to collect plasma samples for liquid chromatography-tandem mass spectrometry (LC/MS-MS) and ELISA method development and establishment of target protein reference ranges in preparation for the biomarker verification work with irradiated and sham-treated NHP samples derived from the planned radiation studies at CiToxLABs in Montreal, Canada.

Samples were collected from these animals over a 4-week period. Male animals were sampled twice weekly, and female animals were sampled once weekly. An average of 12 500-μl aliquots were archived from each male animal and 8 500-μl aliquots were archived from each female animal each week. A total of 48 and 32 aliquots were obtained from each male and female animal, respectively. At the end of the study, animals were transferred back to the NIH contract.

NHP Irradiation Studies (SRI Study M918-12):

A pilot non-GLP irradiation study (SRI study # M918-12, CiToxLAB study #2012-0883) was conducted and completed. The objective of the study was to provide samples for the development of a biomarker panel in blood and saliva of male and female irradiated Rhesus monkeys.

Fifty-four Rhesus monkeys (27M/27F), including 2 spare animals/sex, were received from Pacific Resources (Kunming Biomed International) on Jun. 15, 2012. The age of the animals ranged from 2.5 to 5.1 years. The body weights ranged from 3.4 to 6 kg for males and 3.0 to 4.8 kg for females. Appropriate health assessments were conducted before, following animal receipt, and during the entire course of the study, with animal randomization. The study schedule was staggered. The design for study M918-12 is described in Table 2.

Real-time dosimetry was conducted before the study using a Markus ion chamber with an electrometer and the precision of the delivered dose was determined to be within 1% of the prescribed radiation dose. Nanodots were also placed on the torso (front and back) and the head (frontal and occipital) of the animal for dose verification. Semi-quantitative results from the Nanodots confirmed the dose delivered within ±10% accuracy.

Animals were observed for 7 days post-irradiation. The animals were humanely euthanized on Day 7 before the adverse clinical signs observed after whole body irradiation, except non-irradiated animals (Group 1) re-assigned to Group 6 (see study design in Table 3). Animals in Group 6 were also observed for 7 days post-irradiation and then humanely euthanized.

Following arrival and throughout the course of this study, the animals were observed daily for mortality checks. Detailed exams were performed pre-dose and on Days 1, 3, 5, and 7. Clinical signs were observed twice daily (with particular attention to infections, hemorrhage, and mucositis as well as a diarrhea assessment). Body temperature and food appetence were monitored daily. Body weights were recorded at pre-treatment, on Days 1, 3, 5, and 7. Hematology was performed on all animals at 10 timepoints: Days −3, −2, −1, 1, 2, 3, 4, 5, 6, and 7.

Buccal cells and whole blood samples were collected from animals on 6 occasions; pre-irradiation, post-irradiation (4-12 hours), and on Days 1, 2, 3, and 7.

Hematological results show that animals from all irradiated groups presented a significant decrease in leucocytes, including lymphocyte counts from Day 1 to Day 7 with dose-dependent severity. A decline in neutrophil, white cell, lymphocyte, and platelet counts as well as a decrease in body weights were also observed in the animals exposed to 8 and 10 Gy. Clinical signs noted following irradiation included anorexia, decreased level of activity; vomiting and diarrhea and were more frequently observed at the highest irradiation dose. One female in Group 6 (10 Gy) presented with hypothermia, tremors and severe decreased level of activity and was pre-terminally euthanized on Day 6.

NHP Irradiation Studies (SRI Studies M920-12):

We received plasma samples from CitoxLAB from 32 NHPs exposed to either 2, 5.5, 6.5 Gy of radiation or sham treated. These samples were derived from a study conducted for Chromologic under a BARDA contract. Terminal blood samples were collected on 7 days after irradiation. SRI study number M920-12 was assigned to this study. Collection of blood samples used P100 tube, and the resultant plasma volumes were distributed into multiple aliquots of 0.2 mL and shipped frozen.

Human Patient Studies: Radiotherapy Patients:

In collaboration with Dr. Susan Knox at Stanford University Medical Center (SUMC), samples from human radiotherapy patients continued with the addition of 39 new patient samples that were either whole body (TBI) or partial body (TLI) irradiated. All patients had previously received chemotherapy, but none had received it within 30 days of irradiation. TBI patients received a dose that covered their entire body. TLI patients received a dose that covered the central portion of their body and excluded the head, neck and most of the liver. Data such as patient's age, gender, medical condition, radiation/medical treatment, dose fractions, and hematology were made available to us.

The standard treatment plan for TBI used at the SUMC includes three doses of 120 cGy/d, with each dose separated by ~3 hr for a period of 3 days. The standard treatment plan for TLI patients at Stanford includes single partial-body exposures of 120 cGy/d for ~10 days to major lymphoid tissues while shielding tissues such as the lungs, liver, kidneys, and as much of the bowels as possible. TLI exposures are non-myeloablative, whereas TBI exposures are myeloablative to increase the success rate of bone marrow transplant. In addition, TLI patients receive doses of rabbit anti-thymocyte globulin (ATG) shortly after radiation exposure to suppress T-cells, preparing the patient for transplants. Almost all of the patients had received prior chemotherapy with a variety of alkylating agents.

We collected blood samples before the first radiation treatment, followed by 2 or 3 collection time points, typically 24 hr after each 120-cGy exposure for the TLI patients. Samples from TBI patients were collected pretreatment and ~24 hr after the first and second 360-cGy dose.

Human Confounding Factor Studies:

Collection of blood samples from human patients with confounding conditions included serum samples from 12 patients with serious infections. Since mild infection is a more likely confounding factor in individuals in the event of a mass casualty, we have discontinued collection of samples from patients with serious infections but concentrated on evaluating samples collected from patients with mild infection. Samples from 28 patients with mild infections have been collected and analyzed. Samples from 67 additional trauma patients were also been collected and analyzed.

Immunoassay Methods:

Immunoassays performed utilized either conventional single-plex ELISA or the Luminex multiplex platform. Both assay types are performed in a sandwich format (the analyte to be measured is bound between two primary antibodies—the capture antibody and the detection antibody). In the ELISA the antigen of interest is immobilized via a capture antibody attached to the plate. The antigen is then detected either directly (via a labeled primary antibody) or indirectly (via a labeled secondary antibody). This method is sensitive and robust.

In the Luminex capture antibodies are bound to fluorescent microspheres and binding of analyte is measured by a flow cytometer using a biotinylated detector antibody and phycoerythrin (PE)-coupled streptavidin. When capture antibodies for multiple analytes are conjugated to microspheres with different fluorescent properties, it is possible to simultaneously measure multiple analytes in a single sample. This significant advantage is helpful when sample volumes are limited. Further, the fluorescence-based detection system typically offers greater sensitivity than a colorimetric ELISA.

For each assay, we obtain a standard curve by plotting the signal for each standard concentration (x-axis) against the target protein concentration (y-axis). Using those results, we create a best-fit curve via 4-parameter (ELISA) or 5-parameter (Luminex) regression analysis and calculate the value of the sample of interest using the portion of the standard curve that provides accurate (calculated value compared to actual value) and reproducible results. Samples that have an absorbance value that falls out of the range of the standard curve are tested again after further dilution, and the concentration obtained from the standard curve after analysis of the results is then multiplied by the dilution factor.

UPT Reagent & LFA Methods:

To improve the lateral flow assay (LFA) limit of detection and coefficient of variation (CV), we developed new phosphor reagents by focusing on two variables: (1) creating different size particles, and (2) testing different linker chemistries. We improved upon the process formerly used to generate the UPT particles and can now effectively control the size of the UPT particles. This is accomplished by manipulation of process parameters, specifically the solvent and the total rare earth ion (REI) concentration, utilized to generate the UPT particle precursors. We identified nine smaller phosphors with three unique colors (Table 4).

Several phosphor-antibody conjugation strategies have been investigated. The process involves particle surface functionalization with a cross-linking agent, antibody conjugation, washes to remove unbound antibodies, and finally adjustment of phosphor particle concentration. To determine the optimum method for conjugating antibodies to small phosphors, we employed green phosphors and attached them via four different cross-linkers to antibodies. In addition, we tested three different phosphor-binding-site-to-antibody ratios for each conjugation method. From our analysis, we determined that the best method to conjugate antibodies to phosphors was through a carboxylic acid terminated silane with an antibody-to-binding-site ratio of 20×.

LFA sensitivity depends on the antibody pair selected, materials employed, and buffer components utilized. For our targets of interest, we purchased up to ten different antibodies per target from commercial sources and tested them via ELISA or dot-blots. In our tests, we selected antibody pairs for each target that produced a strong, specific signal and allowed us to differentiate between high and low concentrations of target protein in the range of interest.

To make LFAs that perform optimally with the new phosphors described above, we performed studies to select the best assay materials. We examined three new conjugate release pads and selected G028 as providing the best release and having the most material consistency.

We tested eight new nitrocellulose membranes from Millipore and Whatman and, after some optimization to reduce the phosphor aggregation, selected HF135 for our low-sensitivity assays and HF240 for our high-sensitivity assays. Finally, we examined seven different absorbent pads and found that C048 performed optimally at 15 minutes, providing a target peak amplitude and lower background noise.

Since few assays have been developed using upconverting phosphors, we optimized the non-material conditions of the assay including the conjugate release buffer and running buffer. As one of the main issues is poor release of the phosphors from the conjugate release pad, we focused our efforts there. Our studies included utilizing different buffers, pre-treatment of the conjugate release pad, and direct sonication of the phosphors. Of the numerous studies performed, we found that pulsed-probe sonication of the phosphors provided the largest enhancement of the assay, offering superior release and clearance of the phosphors, which is associated with higher target peaks and better consistency.

LC-MS/MS (& MRM) Methods:

Samples collected in the irradiation studies were analyzed using LC and a tandem mass spectrometer (Orbitrap™ MS/MS). Our LC-MS/MS analysis of samples utilizes a gel-free, quantitative shotgun (bottom-up) LC-MS/MS proteomics approach. In this approach, a specific protease enzyme digests a complex mixture of proteins such as those from plasma samples to produce a mixture of peptides. The peptide mixture is then separated by reversed-phase capillary High-performance LC (HPLC) coupled online to a hybrid Orbitrap mass spectrometer (Thermo Scientific) that has the capability in real chromatographic time to acquire high-resolution, accurate mass measurements of the peptides in full-scan MS mode and obtain sequence information of the peptides in fragmentation MS/MS mode. In this way, thousands of peptides can be profiled and identified simultaneously in a single analysis using automated software packages. While peptide sequence and protein identification are determined through database searching (ByOnic/ComByne, Protein Metrics) to match the observed fragment ions of detected tryptic peptides in MS/MS against standard species-specific protein sequence databases, relative quantitative information is obtained by comparing the corresponding peptide ion current in MS mode across samples (SIEVE, Thermo Scientific). Overall, this represents an efficient and unbiased approach, applied here to identify and quantify candidate radiation-responsive protein biomarkers in plasma. Promising new targets were further tested using immunoassays. When antibodies for immunoassay were not available, a targeted quantitative mass spectrometry method employing isotope-labeled peptide standards, known as multiple reaction monitoring (MRM) with stable isotope dilution, was applied for verification.

Results

LC-MS/MS & MRM Results: NHP Sample LC-MS/MS Analysis:

Sample Preparation Method Development:

We have found that the standard immunodepletion technique for removing highly abundant proteins from plasma samples, allowing for the enrichment of lower abundance proteins, could be successfully carried out in NHP plasma despite the lack of a commercial product designed specifically for NHPs. After testing several commercially available materials designed for abundant-protein depletion in human plasma, the Seppro avian-IgY14 depletion column (Sigma), which is designed to target the 14 most abundant proteins in human plasma, was found to work efficiently for the NHP plasma samples when loading amounts were carefully controlled. The immunodepleted material from this column could also be coupled to a second-stage of immunodepletion known as Supermix, or alternatively subjected to additional protein chromatographic separation, or post-trypsin peptide fractionation to allow us to profile approximately 500 proteins in the NHP plasma, achieving the most in-depth study of an NHP plasma proteome to date. Examples of several lower abundance proteins that are consistently enriched are shown in Table 5.

Candidate Radiation-Responsive Protein Identifications:

Following strategies that we employed in previous mouse studies and the methods developed for NHP, we began our experiments for radiation-responsive protein identifications using pooled materials from samples collected at terminal sacrifice, for which many aliquots are available for detailed analysis. Aliquots were pooled from each of four male animals from the 1-Gy, 4-Gy, 8-Gy, and 10-Gy dose groups (M918 study) so that we could compare directly with the results of 0-Gy control, 1-Gy, 5.5-Gy and 6.5-Gy samples (M920 study, which consisted of males only). Several radiation-responsive proteins were found at varying depths of analysis starting with as little as 3 microliters for analysis of undepleted plasma to 225 microliters of plasma for the more in-depth depletion/fractionation methods. Among those upregulated proteins, AMY1A, CRP, haptoglobin, and alpha-1-antichymotrypsin were readily found in undepleted plasma. For example, signals from multiple peptides assigned to alpha-1-antichymotrypsin increased monotonically as a function of dose up to a final 4-fold increase at Day 7. Additional lower abundance proteins were found to be changing in depleted plasma (for example alpha-amylase and leucine-rich alpha-2-glycoprotein) while deeper depletion revealed other potentially promising new candidate proteins, neutrophil gelatinase-associated lipocalin (NGAL, also known as lipocalin 2), a major salivary gland-derived protein, hypothetical protein LOC695018 (also known as basic salivary proline-rich protein 2), and insulin-like growth factor binding protein 4 (IGFBP4) appeared to be significantly increased. More in-depth plasma fractionation led to additional candidates: regenerating islet-derived protein 3-alpha-like (REG3A), and GDH/6PGL endoplasmic bifunctional protein-like.

Analysis of Individual Plasma Samples:

A subset of early time-point samples from various dose-groups was processed and analyzed to screen for additional early-responding radiation sensitive proteins. We observed that at day 1 two salivary proteins alpha-amylase and basic salivary proline-rich protein 2 were strongly up-regulated (>20-fold).

Identification of Salivary Proteins in Monkey Plasma:

Table 6 lists the major salivary proteins identified in whole saliva for human and monkey. The identifications of the two salivary proteins in NHP plasma samples were confirmed.

Identification of Isoform Specific Changes:

For serum amyloid A (SAA) and salivary amylase, we identified isoform-specific radiation responses, providing detailed information for ELISA assay development.

In summary, we have identified 26 up- and 5 downregulated candidates in plasma (with a cut-off fold change >2 fold) based on our LC-MS/MS analysis of M920 and M918 NHP samples with the developed methods. Results are summarized in Table 7.

Validation/Verification Using MRM Method:

We expanded our LC-MS/MS effort to complement the ELISA analysis for biomarker confirmation by screening a large number of individual samples using a targeted quantitative analysis method, MRM, with isotope-labeled peptide standards. We have previously utilized this method successfully for marker verification/validation of parotid secretory protein (PSP) specific to the salivary gland damage in mice. MRM assays for monkey studies were developed for candidate proteins including amylase, alpha-1 antichymotrypsin, and NGAL et al (Table 8). As a proof-of-concept, we compared our MRM results from alpha-1 antichymotrypsin. Our data show good correlation between the two assay measurements. Similar to ELISA results, a clear trend of up-regulation with the increase of dose was observed. We processed and analyzed 18 batches of samples to include all 300 M918 samples, and 30 M920 samples and quality controls made of a large pool of NHP plasma purchased from Bioreclamation. Examples of assay reproducibility are demonstrated by a batch-to-batch CV of 3.8% for the depletion step and overall CVs of 8 to 26% for the various MRM assays. As part of MRM assay validation study, 6 samples were subjected to entire process from new sample aliquots through sample process and mass spectrometry analysis to evaluate overall assay reproducibility.

Human Sample LC-MS/MS Analysis:

We completed LC-MS/MS analysis of additional sets of plasma samples from radiotherapy patients (both TLI and TBI). Using the IgY top-14 depletion method, we have confirmed upregulations for several our previously reported key responsive proteins. These proteins included AMY1 and salivary acidic proline-rich phosphoprotein 1/2 precursor (PRPC) for the TBI patient samples.

A drastic increase in basic salivary proline-rich protein 2 (PRB2) level by radiation was obtained. The results confirmed the identification of two additional salivary proteins in plasma other than the previously reported alpha-amylase (AMY1) as markers for radiation damage to salivary glands. We have also found that a subset of patients showed upregulation by radiation for cartilage oligomeric matrix protein (COMP). Results from analyzing the human TBI samples are summarized in Table 9.

Immunoassay Results: Both NHP and human sample sets were analyzed using either ELISA or Luminex immunoassays for various panels of proteins, as described herein.

NHP Samples: The NHP sample sets were analyzed in duplicate by immunoassay for up to 33 different proteins. Initial screening studies were performed on the M920 and A246 sample sets to identify the most promising radiation responsive proteins. The more promising proteins from this study were retained in the panels used for analysis of the M918 sample set. The complete list of proteins analyzed in each NHP data set is listed in Table 10 below.

All immunoassays included control samples consisting of pooled NHP plasma (from normal healthy animals) that served as a standard, independent of the normal assay calibration standards used to generate the standard curves. CVs for these plasma control samples are listed in Tables 11 and 12 for two of the key proteins of interest, Flt3L and ACT. The plate-to-plate CVs for the control samples are ~13% for Flt3L (averaged over 15 plates) and ~16% for ACT. The % differences calculated for the replicates on each plate were typically below 10% but were high (>20%) in a few instances for Flt3L.

Box plots for some of the radiation-responsive proteins (measured by immunoassay) were prepared for AMY1A, ACT, IL15, and Flt3L. Heatmaps were prepared showing the results of t-tests performed between the 5 different radiation groups and the control group for 24 different proteins. T-tests were performed by comparing the log 10 of the protein concentrations each radiation group on a given day with the log 10 of the control group protein values measured on the same day. Key radiation responsive proteins include IL15, IL18, MCP1, ACT, Flt3L, serum amyloid A, APOA4, hemopexin (HPX), NGAL, and salivary amylase (due to the lack of good commercial immunoassay kits for APOA4, HPX, and salivary amylase, these proteins were measured using MRM rather than immunoassay).

Human Samples: Human data sets were analyzed primarily for 13 different proteins that included Flt3L, CRP, clusterin, elastase, salivary amylase, IL15, haptoglobin, alpha fibrinogen, TNC, MCP1, SAP, GCSF, and IL18. The heatmap showed paired and un-paired (versus controls)

t-tests performed on the TBI sample set and indicates the proteins that are likely radiation responsive (p-value <0.01 on either day 1, 2, or 3). For the TBI patients, these include Flt3L, salivary amylase, IL15, haptoglobin, MCP1, and TNC.

Box plots for two of the more important radiation responsive proteins, Ftl3L and salivary amylase, show the log 10 of the plasma protein concentrations for, from left to right, the control samples, mild infection, severe infection, trauma, and TBI patients. The data reveal that both are excellent markers for the TBI patients—Flt3L is clearly elevated on Days 2 and 3, and salivary amylase is clearly elevated on all days post irradiation. Flt3L is perhaps mildly elevated in the trauma patients but not the mild infection patients. Salivary amylase levels in both mild infection and trauma patients are not significantly different from the controls. These results reinforce our finding that Flt3L and salivary amylase are excellent markers of total radiation exposure in human, consistent with the results obtained with various classifiers as discussed below.

LFA Results: We developed single-plex and duplex assays for four different biomarkers that increase following radiation exposure in either non-human primates and/or humans. These include AMY1A, TNC, CRP, and Flt3L. The single-plex UPT-LFA for AMY1A was developed first. For this assay, there is a 5.5-fold increase in signal from a healthy level (10 ng/mL in 10% plasma) to and irradiated level (100 ng/mL in 10% plasma).

The plasma concentration of CRP is normally between 0.5 and 10 ug/mL, rising into the 100s of ug/mL with radiation exposure (in TLI patients). To develop our CRP LFA, we built an inhibition-style assay to avoid the hook effect that would inevitably arise at the high levels of CRP caused by radiation exposure.

Healthy humans have an average Flt3L plasma concentration of 113 pg/mL, and this can increase up to 1000 pg/mL with radiation exposure. Thus, for the Flt3L LFA development, we aimed to create a high-sensitivity assay. To do this, we selected a sandwich-style assay and employed Yb/Tm $Y_2O_2S$ phosphors that have a bright signal at 800 nm.

Additionally, we developed duplex assays for AMY1A/CRP and Flt3L/TNC. We tested our AMY1A/CRP duplex assay on a grid of thirty-six samples with six different concentrations of AMY1A and six different concentrations of CRP over the range of concentrations applicable to healthy and irradiated patients in 5% plasma. We found that the duplex assay gave good differentiation between low and high levels of AMY1A and CRP, and that measurement of AMY1A and CRP were relatively independent of each other. Further, we calculated the CVs of the duplex AMY1A and CRP measurements. The CVs of the AMY1A measurement were below 8%, while the CRP measurement varied more, having CVs below 13%. In initial work we developed and optimized four functioning LFAs for measurement of CRP, AMY1A, TNC and Flt3L and two duplex assays for CRP/AMY1A and Flt3L/TNC.

Data Analysis: NHP Samples. Our Irradiation Study (M918-12) contained 6 dosage groups with 10 animals in each group at 5 timepoints for a total of 300 plasma samples. Of the 300 samples, 180 were below 4 Gy and 120 samples were at or above 4 Gy. In addition we received 30 government-provided samples (M920-12) of animals exposed to 0, 2, 5.5, or 6.5 Gy of irradiation. The samples were collected at Day 7 after irradiation. We determined the concentration level of 24 different proteins using ELISA, Luminex, or MRM in each of the 330 samples.

For each group and time point (10 animals total), we determined the group mean, standard deviation, maximum value, and minimum value. Table 13 shows representative date for one protein (Flt3L) at a single time point (Day 7). In addition, we created box plots to visualize the radiation response of a single protein across all groups and time points. Finally, we performed t-tests on the log base 10 of the protein concentrations between each irradiation group and the 0-Gy control group for all time points. We determined that all the proteins were well described by a log-normal distribution using quantile-quantile plots. Table 14 shows the p-values for each group and time point compared to the 0 Gy group at the same time point.

In addition to looking at single protein response, we combined multiple proteins together to generate exposure classifiers, including 7 iterations of 5-fold cross validation to test different combinations of protein as predictors of the high (≥4 Gy) or low (<4 Gy) exposure class. We used primarily three different statistical learning algorithms: (1) conditional inference trees, (2) support vector machines (SVM), or (3) logistic regressions. Qualitatively, the classifiers performed comparably in terms of general accuracy, importance of specific proteins to accuracy rates, and had similar samples consistently misclassified. Table 15 shows accuracy, false-negative, and false-positive rates for different combinations of proteins using logistic regression, SVM, or conditional-inference tree statistical learning algorithms.

Since the classifiers performed equally well, we selected logistic regressions for further analysis, primarily because the output is the probability of a sample belonging to the high-dose or low-dose group. Table 15 shows the logistic regression classifier results for a representative set of high scoring protein panels. It is important to notice that Flt3L and ACT are generally included in the best performing panels; however, a number of other proteins (CRP, IL15, MCP1, NGAL, AMY1A, and HP) can be used interchangeably to yield comparable results. The additional proteins will serve as risk mitigation as we additional confounding studies.

One of the top panels was ACT, AMY1A, IL15, and Flt3L. Table 16 shows the accuracy, sensitivity, specificity, positive predictive value, negative predictive value, false positive rate and false negative rate of the panel for the 300 samples using 5-fold cross validation with a probability of exposure cutoff of 30%. We plotted the probability of exposure as a function of dose and showed the receiver operator characteristic curve for the data set as the cutoff probability for exposed classification is adjusted from 100% to 0%. The area under the curve (AUC) for this panel is 0.985. On average, this panel classifies 290 of the 300 samples correctly. Table 17 shows the 4 common false negative samples. Table 18 shows the 6 common false positive samples. For validation of our mode we developed a classification model based on the primary irradiation study (M918) and predicted the class of 30 samples provided by the government (M920) from a different study. These animals were exposed to different high doses (5.5 and 6.5 Gy) and a different overall protocol in a second study. The model from the M918 study classified 27 of the 30 samples correctly, with 0 false negatives and 3 false positives (30% probability of exposure). We chose 30% probability of exposure to bias false positives over false negatives. Additionally we were able to validate a subset of our model (ACT, FLT3L, and IL15) against samples from our A246 study. The A246 study were blood draws from 28 older NHPs over a period of 4 weeks. These animals didn't receive any gamma irradiation and therefore are equivalent to control animals. We didn't have data on AMY1A for these animals. Using a subset of the biomarker panel and the M918 samples for training we were able to predict with 100% 74 samples as not exposed. The highest probability of exposure for these 74 samples was 0.3%, again validating our use of ACT, FLT3L, and IL15 as radiation biomarkers.

Human Samples.

As discussed previously, t-tests performed on the human sample immunoassay data indicated the key radiation-responsive proteins in TBI patient samples included primarily Flt3L, AMY1A, IL15, Haptoglobin, MCP1, and TNC. Data showed the separation that can be obtained between the TBI and control samples using just two proteins, Flt3L and AMY1A, without using any classifiers. Just these two proteins provide excellent discrimination between the TBI (>2.4 Gy) and TBI (0 Gy)+ control groups.

Using AMY1A, Flt3L, and IL15 in a logistic regression classifier using 10 iterations of a 5-fold cross-validation yields a classification accuracy of 95.7%, with false-negative and -positive rates of 7% and 3.2% respectively (using a 50% cutoff threshold). Similar accuracies can be obtained by substituting MCP1 for either IL15 or Flt3L. We plotted the exposure probabilities for each of 5 groups of samples (controls, mild infection, trauma, TBI unexposed, and TBI irradiated ≥2.4 Gy), computed by logistic regression using the AMY1A, Flt3L, IL15 protein panel. By varying the cutoff threshold continuously and computing the TP, FP, TN, and FN (and thus the sensitivity and specificity) for each case, one can generate the receiver operating characteristic (ROC) curve. As was the case with the NHP data, this is an exceptional ROC curve—the total area under the curve is 0.98. A satisfying feature of these results are that the human panel uses 3 of the same 4 proteins in the NHP panel.

A discrepancy between the human TBI data and the NHP (and murine in the case of CRP) model is that neither CRP nor ACT are observed to be radiation responsive. A review of the literature indicates that elevated CRP levels have been observed in (presumably previously healthy) Chernobyl accident victims [Mal'tsev et al., 2006], and also that CRP levels in TBI patients do not appear to elevate during radiation treatment [van der Velden et al., 2010]. We know there are four key differences between the animal and human TBI models: (1) irradiation protocol (the TBI patients receive lower, fractionated doses versus a high, single acute dose), (2) the health state (TBI patients are gravely ill versus healthy animals), (3) previous treatment exposures (the TBI patients received chemotherapy to destroy cancer cells versus no treatment) and (4) sample time collections (TBI patient samples are always collected 1 day after a fractionated radiation therapy versus the animal models that have samples collected at day 1, 2, 3, and 7 post-acute exposure). Given the significant differences between the models there are many possible explanation for the differences and we believe the NHP model is more representative for our diagnostic device.

Reader Systems: We built and tested three reader devices for reading UPT lateral flow assays. The alpha system consists of a 980-nm laser locked by a fiber Bragg grating. The 980-nm beam is focused to a 300-μm spot using an a spherical lens. Two microelectromechanical systems (MEMS) mirrors are used to select the wick to be analyzed in the LFA holder and raster across the entire 30 mm of the selected wick. The wick is imaged using an f/2.8 5 mm effective focal length lens from ThorLabs. The sensor is a charge-coupled device (CCD) camera with a bandpass filter to reject the 980 nm excitation laser light. We developed custom printed circuit boards to implement discretionary access control (DAC) of the MEMS mirrors, laser drivers, and thermoelectric cooler (TEC) drivers. The entire system is controlled by a Gumstix processor with touch screen liquid crystal display (LCD). Additionally the gumstix processor controls a Quick Response (QR) code reader that loads a standard curve from a QR code printed on the wick housing.

We tested the repeatability of the reader system and LFA in the last option. We developed LFA for AMY1A and Flt3L. In order to test the repeatability of the assay, we striped 12 wicks with AMY1A capture antibodies and 12 wicks with Flt3L capture antibodies. We tested 4 different concentrations of AMY1A analyte: 5, 25, 50 and 100 ng/ml and 4 different concentrations of Flt3L analyte: 0.002, 0.1, 0.5, and 1 ng/ml. We tested each concentration in triplicate; additionally, we repeated the entire stripping and LFA process on three different days, for a total of 36 tests for each analyte. We determined the intraday and interday coefficient of variation (CVs) for all the samples. Table 19 shows the resulting CVs. Overall the CVs were better for our Flt3L LFA (less than 10% in all instances) than for the AMY1A assay (less than 13% in all instances). Typically the CVs were worse at higher concentrations than lower concentration. We also measured the two AMY1A wicks (5 and 50 ng/ml) 15 times, each time removing and re-inserting the wick. The instrument CV for these two wicks was 0.84% and 1.6%. The results are shown in Table 20.

Figure 1A:
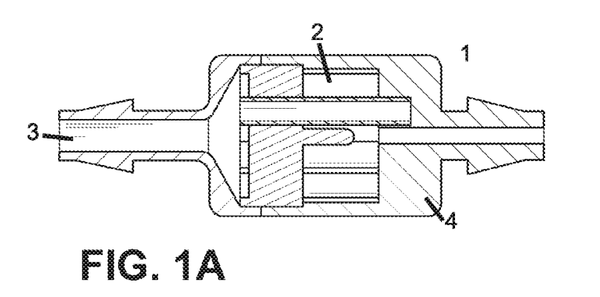
Figure 1B:
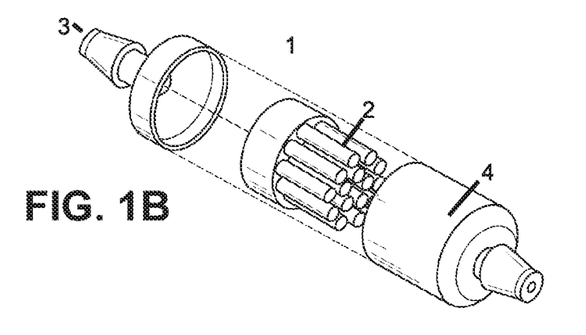
Figure 2:
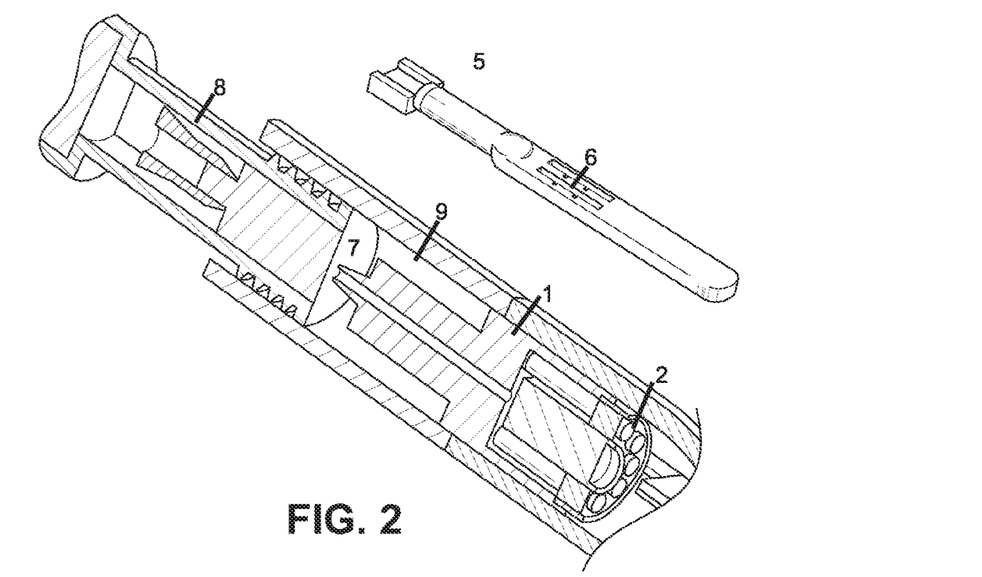
FIG. 2. The internal features of the sample filtering device. The inset shows the entire device connected to a lateral flow strip.

We also developed sample collector device, including a hollow-fiber filter approach that provides a cleaner (less cell lysis and greater cell removal) at a lower pressure than traditional flat filter devices. FIG. 1 shows a schematic of the hollow-fiber filter function. FIG. 2 shows a concept of the final integrated device. FIG. 1. (a) A schematic of the hollow fiber tube separation embodiment. The whole blood mixed with LFA running buffer is pushed into an inline filter 1 that contains the hollow fiber tubes 2. The pore size of the hollow fiber tubes is ~650 nm, which allows plasma through but not cells. The resulting plasma is collected at the output. FIG. 1. (b) A solid works schematic of the filter assembly. The entire chamber 4 now has a dead volume of 60 ul. FIG. 2. The internal features of the sample filtering device. The inset 5 shows the entire device connected to a lateral flow strip 6. The running buffer dilutes the collected whole blood and is held back by a foil seal 7. The plunger 8 travels down the chamber 9 and the foil seal 7 is pierced allowing the running buffer to move down the sample via to the hollow fiber tube separation device 1. The hollow fiber tubes separate the plasma and running buffer mixture from the blood cells. We tested 10 of the final prototype filter design on samples of mouse blood. The samples were diluted with 210 μL of phosphate buffered saline (PBS) (to simulate our final running buffer at a 5% plasma concentration) and spiked with human Flt3L at 210 ng/ml concentration. The volume recovery, cell passage, cell lysis, and Flt3L concentration in the resulting plasma are shown in Table 21. In the instances of cell passage, cell lysis, and Flt3L, our devices performed better than the control in which plasma was collected by traditional centrifugation.

Discussion

Our studies have demonstrated the feasibility of plasma protein biomarker panels in the NHP model for distinguishing between equivalent human radiation exposures of above and below 2 Gy (4 Gy in the NHP model). Our best results were obtained with a panel of 4 proteins: ACT, Flt3L, AMY1A, and IL15. Using these 4 proteins, a logistic regression classifier, which assigns an exposure probability to each of 300 samples in our M918 baseline study set, achieves an average classification accuracy of 96.5% using 5-fold cross validation over 7 iterations. Using the M918 data as a training set, we also tested the classifier on NHP samples obtained from a two separate studies and achieved excellent classification accuracy with no false negatives and only 3 false positives.

A subset of this panel, namely the 3 proteins Flt3L, AMY1A, and IL15, can be used to classify a data set containing 104 human TBI samples (36 pre-irradiation and 68 post-exposure at ≥2.4-Gy cumulative dose) plus 82 human control samples with an accuracy of 95.7% with false-negative and -positive rates of 7% and 3.2% respectively (using a 50% cutoff threshold). Furthermore, the classification accuracy is not degraded significantly if samples from trauma and mild infection patients are included in the data set. In view of the fact that the TBI patients are seriously ill (many have leukemia or other blood cancers), are immunocompromised (they have received many immunosuppressive drugs as part of their previous chemotherapeutic treatments), and have received fractionated (rather than single acute) radiation doses, the overlap between the human and NHP protein panels is a remarkable result. Given these results, we consider the panel of 4 proteins, ACT, Flt3L, AMY1A, and IL15 as a preferred baseline biomarker panel.

We have also demonstrated lateral flow assays that are sensitive enough to detect two of the targets from the above panel (AMY1A and Flt3L) in addition to two other radiation responsive proteins (TNC and CRP). We also demonstrated duplexed assays with AMY1A/CRP and Flt3L/TNC. An alpha prototype reader system was designed, and 3 units were built and tested. We demonstrated a repeatability of <2% on multiple reads of an LFA test strip. In addition, a novel sample collection tool was developed and a 2-component design has been produced that collects a finger-prick blood sample, mixes a metered amount of blood with a buffer solution, and applies the sample to a dual lateral flow strip cassette.

REFERENCES

Akashi, M., et al. (2001), Initial symptoms of acute radiation syndrome in the JCO criticality accident in Tokai-mura, *J Radiat Res*, 42 Suppl, S157-166.

Barrett, A., A. Jacobs, J. Kohn, J. Raymond, and R. L. Powles (1982), Changes in serum amylase and its isoenzymes after whole body irradiation, *Br Med J (Clin Res Ed)*, 285(6336), 170-171.

Bertho, J. M., and L. Roy (2009), A rapid multiparametric method for victim triage in cases of accidental protracted irradiation or delayed analysis, *Br J Radiol*, 82(981), 764-770.

Bertho, J. M., et al. (2001), Level of Flt3-ligand in plasma: a possible new bio-indicator for radiation-induced aplasia, *Int J Radiat Biol*, 77(6), 703-712.

Blakely, W. F., D. J. Sandgren, V. Nagy, S. Kim, and N. Ossetrova (2011), Murine partial-body radiation exposure model for biodosimetry studies—preliminary report, *Radiation measurements*, 46, 898-902.

Blakely, W. F., N. I. Ossetrova, M. H. Whitnall, D. J. Sandgren, V. I. Krivokrysenko, A. Shakhov, and E. Feinstein (2010), Multiple parameter radiation injury assessment using a nonhuman primate radiation model-biodosimetry applications, *Health Phys*, 98(2), 153-159.

Brattstrom, C., J. Tollemar, O. Ringden, K. Bergstrom, and G. Tyden (1991), Isoamylase levels in bone marrow transplant patients are affected by total body irradiation and not by graft-versus-host disease, *Transpl Int*, 4(2), 96-98.

Cao, S., A. B. Troutt, and Y. M. Rustum (1998a), Interleukin 15 protects against toxicity and potentiates antitumor activity of 5-fluorouracil alone and in combination with leucovorin in rats bearing colorectal cancer, *Cancer Res*, 58(8), 1695-1699.

Cao, S., J. D. Black, A. B. Troutt, and Y. M. Rustum (1998b), Interleukin 15 offers selective protection from irinotecan-induced intestinal toxicity in a preclinical animal model, *Cancer Res*, 58(15), 3270-3274.

Christensson, A., T. Bjork, O. Nilsson, U. Dahlen, M. T. Matikainen, A. T. Cockett, P. A. Abrahamsson, and H. Lilja (1993), Serum prostate specific antigen complexed to alpha 1-antichymotrypsin as an indicator of prostate cancer, *J Urol*, 150(1), 100-105.

Cowland, J. B., and N. Borregaard (1997), Molecular characterization and pattern of tissue expression of the gene for neutrophil gelatinase-associated lipocalin from humans, *Genomics*, 45(1), 17-23.

Dubray, B., T. Girinski, H. D. Thames, A. Becciolini, S. Porciani, C. Hennequin, G. Socie, M. Bonnay, and J. M. Cosset (1992), Post-irradiation hyperamylasemia as a biological dosimeter, *Radiother Oncol*, 24(1), 21-26.

Guipaud, O., and M. Benderitter (2009), Protein biomarkers for radiation exposure: towards a proteomic approach as a new investigation tool, *Ann 1st Super Sanita*, 45(3), 278-286.

Hong, J. H., C. S. Chiang, I. L. Campbell, J. R. Sun, H. R. Withers, and W. H. McBride (1995), Induction of acute phase gene expression by brain irradiation, *Int J Radiat Oncol Biol Phys*, 33(3), 619-626.

Junglee, D., A. Katrak, J. Mohiuddin, H. Blacklock, H. G. Prentice, and P. Dandona (1986), Salivary amylase and pancreatic enzymes in serum after total body irradiation, *Clin Chem*, 32(4), 609-610.

Lai, Y. G., V. Gelfanov, V. Gelfanova, L. Kulik, C. L. Chu, S. W. Jeng, and N. S. Liao (1999), IL-15 promotes survival but not effector function differentiation of CD8+ TCRalphabeta+ intestinal intraepithelial lymphocytes, *J Immunol*, 163(11), 5843-5850.

Lilja, H., A. Christensson, U. Dahlen, M. T. Matikainen, O. Nilsson, K. Pettersson, and T. Lovgren (1991), Prostate-specific antigen in serum occurs predominantly in complex with alpha 1-antichymotrypsin, *Clin Chem*, 37(9), 1618-1625.

Lugering, N., T. Kucharzik, C. Maaser, M. Kraft, and W. Domschke (1999), Interleukin-15 strongly inhibits interleukin-8 and monocyte chemoattractant protein-1 production in human colonic epithelial cells, *Immunology*, 98(4), 504-509.

Mal'tsev, V. N., A. A. Ivanov, V. F. Mikhailov, and V. K. Mazurik (2006), [The individual prognosis of the gravity and of the outcome of acute radiation disease based on immunological indexes], *Radiatsionnaia biologiia, radioecologiia/Rossiiskaia akademiia nauk*, 46(2), 152-158.

Noto, A., F. Cibecchini, V. Fanos, and M. Mussap (2013), NGAL and Metabolomics: The Single Biomarker to Reveal the Metabolome Alterations in Kidney Injury, *Biomed Res Int*, 2013, 612032.

Ossetrova, N., D. J. Sandgren, and W. F. Blakely (2011), C-reactive protein and serum amyloid A as early phase and prognostic indicators of acute radiation exposure in nonhuman primate total-body irradiation, *Radiation measurements,* 46, 1019-1024.

Ossetrova, N. I., and W. F. Blakely (2009), Multiple blood-proteins approach for early-response exposure assessment using an in vivo murine radiation model, *Int J Radiat Biol,* 85(10), 837-850.

Ossetrova, N. I., D. J. Sandgren, S. Gallego, and W. F. Blakely (2010), Combined approach of hematological biomarkers and plasma protein SAA for improvement of radiation dose assessment triage in biodosimetry applications, *Health Phys,* 98(2), 204-208.

Ossetrova, N. I., A. M. Farese, T. J. MacVittie, G. L. Manglapus, and W. F. Blakely (2007), The use of discriminant analysis for evaluation of early-response multiple biomarkers of radiation exposure using non-human primate 6-Gy whole-body radiation model, *Radiation Measurements,* 42, 1158-1163.

Patel, S., F. H. Wang, T. L. Whiteside, and U. Kasid (1998), Ionizing radiation and TNF-alpha and stimulated expression of alpha1-antichymotrypsin gene in human squamous carcinoma cells, *Acta Oncol,* 37(5), 475-478.

Prat, M., C. Demarquay, J. Frick, D. Thierry, N. C. Gorin, and J. M. Bertho (2005), Radiation-induced increase in plasma Flt3 ligand concentration in mice: evidence for the implication of several cell types, *Radiat Res,* 163(4), 408-417.

Prat, M., C. Demarquay, J. Frick, N. Dudoignon, D. Thierry, and J. M. Bertho (2006), Use of flt3 ligand to evaluate residual hematopoiesis after heterogeneous irradiation in mice, *Radiat Res,* 166(3), 504-511.

Reinecker, H. C., R. P. MacDermott, S. Mirau, A. Dignass, and D. K. Podolsky (1996), Intestinal epithelial cells both express and respond to interleukin 15, *Gastroenterology,* 111(6), 1706-1713.

Roudkenar, M. H., Y. Kuwahara, T. Baba, A. M. Roushandeh, S. Ebishima, S. Abe, Y. Ohkubo, and M. Fukumoto (2007), Oxidative stress induced lipocalin 2 gene expression: addressing its expression under the harmful conditions, *J Radiat Res,* 48(1), 39-44.

Sharma, M., and J. E. Moulder (2013), The urine proteome as a radiation biodosimeter, *Adv Exp Med Biol,* 990, 87-100.

Shiiba, M., et al. (2013), Lipocalin-2 is associated with radioresistance in oral cancer and lung cancer cells, *Int J Oncol,* 42(4), 1197-1204.

Sugihara, T., H. Murano, M. Nakamura, and K. Tanaka (2013), In vivo partial bystander study in a mouse model by chronic medium-dose-rate gamma-ray irradiation, *Radiat Res,* 179(2), 221-231.

van der Velden, W. J., A. H. Herbers, T. Feuth, N. P. Schaap, J. P. Donnelly, and N. M. Blijlevens (2010), Intestinal damage determines the inflammatory response and early complications in patients receiving conditioning for a stem cell transplantation, *PLoS ONE,* 5 (12), e15156.

Zhang, Y., C. Guo, H. Zhang, and S. Dong (2009), Synergistic protecting effect of cord blood CD34+ cells over-expressing both interleukin-3 and Flt3 ligand on lethally irradiated mice, *Int J Hematol,* 90(1), 64-73.

The invention encompasses all combinations of recited particular and preferred embodiments. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

TABLE 1

Summary data on key radiation responsive proteins observed in this study.

| Protein | Normal Expression | Regulation | Function | Radiation Response | References | Potential Confounders |
|---|---|---|---|---|---|---|
| Salivary alpha amylase (AMY1A) | Highly expressed in salivary gland, may also be in lung macrophages, exocrine pancreas, and thyroid. | Regulated by 1-methylspermidine, FGF19, MBD2, PSEN1, SAT1, progesterone | Carbohydrate metabolism | Up-regulated ~1 day after radiation exposure Indicative of injury to parotid gland Known to be up-regulated in irradiated mice, NHPs, and humans. | (1) Kashima, H. K., Kirkham, W. R., Andrews, J. R., Am. J. Roentgenol, 94, 271-291. (2) Blakely et. al. Radiation Measurements 42 (2007) 1164-1170 | Injury to the parotid gland; sarcoidosis |
| fms-related tyrosine kinase 3 ligand (Flt3L) | Expressed by marrow stromal cells. | Expression is known to be regulated by cytokines: IL-2, IL-7, & IL-15 | Stimulates proliferation and differentiation of various blood cell progenitors: dendritic cells, myeloid cells, T and B cells | Up-regulated ~3 days after radiation exposure Stimulates production of blood cells Bone marrow biomarker and biomarker in radiation-induced aplasia | (1) Kenins, et.al. Journal of Experimental Medicine, Vol. 205, No. 3, Mar. 17, 2008 523-531 (2) Blakely et.al. Radiation Measurements 46 (2011) 898e902 | Parasitic infections, rheumatoid arthritis |
| Neutrophil-gelatinase associated lipocalin (NGAL, LCN2) | Highly expressed in the cytoplasm of lymphoid cells in the spleen, bone marrow and neutrophils, cytoplasmic and glandular cells of the cervix. Also expressed in kidney, heart, lung, testis and liver parenchymal cells | Regulated by pro-inflammatory cytokines including IL-1, TNF with IL-7 which drives the activation/binding of NFκB and it's associated factor, to it's promoter site, upregulating its expression. Also forms heterodimer; disulfide-linked with MMP9. | Iron-trafficking protein involved in innate immunity, apoptosis, and renal development; sequesters iron to limit bacterial growth | Up-regulated on days 1-3 following radiation exposure Increase may be due to action of pro-inflammatory cytokines Up-regulated mRNA in irradiated primary normal liver, heart, kidney cells and linked toradioresistance in oral and lung carcinoma cell lines. | (1) Karlson et.al. Journal of Biological Chemistry, 285, 19, pp. 14088-14100, May 7, 2010 (2) Fukumoto et al., J. Radiation Res., 48, pp. 39-44, 2007. | NGAL is elevated in kidney injury and is, therefore, reported to be a good biomarker for kidney function |
| Alpha-1-antichymotrypsin (ACT, SERPINA3) | Plasma protein, mainly synthesized in liver, also in epithelial cells of the cerebral cortex, lung macrophages, kidney tubules | Regulated by IL-6, TNF, IL-1, IL-22 and STAT3 | Protease inhibitor protects tissues from excess proteolytic activity. Acute phase response protein induced by inflammation | Up-regulated on days 1-3 following radiation exposure Increase may be due to action of pro-inflammatory cytokines | ACT was up-regulated in cerebral tissues in mice after >7 Gy whole body or head only irradiation (1) Hong et al, IJROBP, 1995 | Alzheimer's disease, Huntington's disease, Parkinson's disease |
| Interleukin 15 (IL15) | Cytokine widely expressed by epithelial cells, stromal cells, and immune cells such as dendritic cells, monocytes and macrophages. | Stimulated by cytokines such as GM-CSF, IFNγ or toxins such as LPS | Regulates T and natural killer cell activation and proliferation | Upregulated on days 1-7 following radiation exposure Increase may be due to action of pro-inflammatory cytokines | (1) Fehniger, T. and Caligiuri, M. Blood, 2001 97: 14-32 (2) Melenhorst JJ, et al., Haematologica 2012; 97(6): 867-873. | Inflammatory bowel disease, multiple sclerosis, hepatitis C, T-cell leukemias & lymphomas. |

TABLE 2

M918-12 NHP Irradiation study design.

| Group | Target Radiation Dose Level (Gy) | Approximate Radiation Dose Rate (Gy/min) | Number of Animals Males | Number of Animals Females |
|---|---|---|---|---|
| 1 | 0 | 0.60 | 5 | 5 |
| 2 | 1 | | 5 | 5 |
| 3 | 2 | | 5 | 5 |
| 4 | 4 | | 5 | 5 |
| 5 | 8 | | 5 | 5 |

TABLE 3

Group 6 M918-12 study design.

| Group | Radiation Dose Level (Gy) | Approximate Radiation Dose Rate (Gy/min) | Number of Animals Males | Number of Animals Females |
|---|---|---|---|---|
| 6 | 10 | 0.60 | 5 | 5 |

TABLE 4

Upconverting phosphor nanoparticle sets.

| ID | Material | Precursor | Activation *C | Size, nm |
|---|---|---|---|---|
| P1 | Yb/Er Y202S | BARDA-01 | 1350 | 300 |
| P2 | Yb/Er Y202S | BARDA-09 | 1350 | 190 |
| P3 | Yb/Er Y202S | BARDA-12 | 1350 | 250 |
| P4 | Yb/Er Y202S | BARDA-17 | 1350 | 150 |
| P5 | Yb/Er Y202S | BARDA-18 | 1350 | 190 |
| P6 | Yb/Er Y202S | BARDA-20 | 1350 | 180 |
| P7 | Yb/Er Y202S | BARDA-20 | 1450 | 180 |
| P8 | Yb/Er Y202S | BARDA-27 | 1450 | 150 |
| P9 | Yb/Er Y202S | BARDA-28 | 1450 | 190 |
| P10 | Yb/Er Y202S | BARDA-21 | 1400 | 150 |

TABLE 5

A list of some lower abundance proteins that showed consistently enrichment in pooled monkey plasma using the IgY antibody depletion/fractionation techniques.

| | |
|---|---|
| Glutathione peroxidase | cholesteryl ester transfer protein-like |
| Mannan-binding lectin serine protease 1 | cysteine-rich secretory protein |
| Transmembrane glycoprotein NMB | intelectin-1-like |
| Extracellular matrix protein 1 | filamin-A |
| Thyroxine-binding globulin | CD109 antigen-like isoform 1 |
| Hyaluronan-binding protein 2 | cathepsin D isoform 3 |
| sulfhydryl oxidase 1-like protein | coactosin-like protein-like isoform 2 |
| hepatocyte growth factor activator-like protein | neural cell adhesion molecule 1 |
| insulin-like growth factor-binding protein | carbonic anhydrase 1 |
| Adiponectin | cystatin-C |
| pigment epithelium-derived factor-like protein | 14-3-3 protein zeta/delta-like isoform |
| Biotinidase | Intercellular adhesion molecule 1 (ICAM1) |
| von Willebrand factor | beta-2-microglobulin (B2MG) |
| galectin-3-binding protein | |

TABLE 6

Lists of the major proteins identified in whole saliva for confirmation of salivary protein sequences in NHP compared to human.

| Top Proteins Identified in NHP Saliva | Top Proteins Identified in Human Saliva |
|---|---|
| alpha-amylase | salivary alpha-amylase |
| cystatin-S (Cystatin-4), cystatin-D (Cystatin-5), cystatin-B | cystatin-1, -2 and -4 |
| hypothetical protein LOC722356 (similar to salivary acidic proline-rich phosphoprotein 1/2 for human) | proline-rich protein HaeIII subfamily 2 (also known as salivary acidic proline-rich phosphoprotein 1/2) |
| hypothetical protein LOC695018 (also known as basic salivary proline-rich protein 2) | basic salivary proline-rich protein 1 and 2 |
| mucin-19 | mucin-5B |
| short palate, lung and nasal epithelium carcinoma-associated protein 2 and bactericidal/permeability-increasing (BPI) fold-containing family B member 1 (also known as long palate, lung and nasal epithelium carcinoma-associated protein 1) | prolactin-inducible protein |
| carbonic anhydrase 6 | carbonic anhydrase |

TABLE 7

Radiation responsive protein candidates identified and quantified using digested monkey plasma samples (shotgun gel-free method).

| Protein Name | Dose | Day | Up or Down | Max Fold Change Observed |
|---|---|---|---|---|
| amyloid A protein isoform 1 or 2 (SAA1 or SAA2) | 10 Gy | 7 | Up | >200* |
| c-reactive protein (CRP) | 10 Gy | 7 | Up | >100* |
| regenerating islet-derived 3 alpha (REG3A) | 8 or 10 Gy | 7 | Up | >20* |
| insulin-like growth factor binding protein 4 (IGFBP4) | 8 or 10 Gy | 7 | Up | >20* |
| alpha-amylase | 8 or 10 Gy | 1 | Up | >20* |
| basic salivary proline-rich protein | 8 or 10 Gy | 1 | Up | >10* |
| haptoglobin (HP) | 10 Gy | 7 | Up | >10* |
| alpha-1-antichymotrypsin | 10 Gy | 7 | Up | 7.1* |
| alpha-1-acid glycoprotein 1 or 2 | 10 Gy | 7 | Up | 5.6* |
| GDH/6PGL endoplasmic bifunctional protein (GDH) | 8 or 10 Gy | 7 | Up | >5* |
| cystatin-B (CSTB) | 8 or 10 Gy | 7 | Up | >5* |
| lymphatic vessel endothelial hyaluronic acid receptor 1 (LYVE1) | 6.5 Gy | 8 | Up | ~5* |

TABLE 7-continued

Radiation responsive protein candidates identified and quantified using digested monkey plasma samples (shotgun gel-free method).

| Protein Name | Dose | Day | Up or Down | Max Fold Change Observed |
|---|---|---|---|---|
| neutrophil gelatinase-associated lipocalin (NGAL, aka lipocalin 2, LCN2) | 8 or 10 Gy | 7 | Up | ~5* |
| lipopolysaccharide-binding protein (LBP) | 10 Gy | 7 | Up | ~3.5* |
| angiotensinogen (AGT) | 10 Gy | 7 | Up | 3.2* |
| leucine-rich alpha-2-glycoprotein (LRG1) | 10 Gy | 7 | Up | 3.2* |
| hemopexin-like (HPX) | 10 Gy | 7 | Up | 2.9* |
| complement component C9 (C9) | 10 Gy | 7 | Up | 2.6* |
| fibrinogen (FGA, FGB, FGG) | 10 Gy | 7 | Up | 2.3* |
| inter-alpha-trypsin inhibitor heavy chain H4 (ITIH4) | 10 Gy | 7 | Up | 2.3* |
| inter-alpha-trypsin inhibitor heavy chain H3 (ITIH3) | 10 Gy | 7 | Up | 2.1* |
| complement C5 (C5) | 10 Gy | 7 | Up | 1.8* |
| complement C3, partial (C3) | 10 Gy | 7 | Up | 1.8* |
| complement C4 (C4A, C4B) | 10 Gy | 7 | Up | 1.9* |
| alpha-1-antitrypsin isoform 4 (SERPINA1) | 10 Gy | 7 | Up | 1.9* |
| catalase isoform 2 (CAT) | 6.5 Gy | 8 | Up | ~2* |
| apolipoprotein A-IV (APOA4) | 10 Gy | 7 | Down | ~−10* |
| galectin-3-binding protein isoform 3 (LGALS3BP) | 6.5 Gy | 8 | Down | −4* |
| gelsolin (GSN) | 10 Gy | 7 | Down | −3.1* |
| iduronate 2-sulfatase isoform 4 (IDS) | 6.5 Gy | 8 | Down | ~−2* |
| properdin-like (aka Complement factor P, CFP) | 6.5 Gy | 8 | Down | ~−2* |

TABLE 8

Stable isotope peptides used for target validation by LC-MS/MS in NHP - close the loop when an ELISA assay is not available.

| Protein | Peptide# |
|---|---|
| alpha-amylase | 1 |
| alpha-amylase | 2 |
| alpha-amylase | 3 |
| Proline-rich salivary basic protein | 4 |
| Antichymotrypsin | 5 |
| Antichymotrypsin | 6 |
| Hemopexin | 7 |
| Hemopexin | 8 |
| GDH/6PGL endoplasmic bi functional | 9 |
| GDH/6PGL endoplasmic bi functional | 10 |
| NGAL | 11 |
| Cystatin B | 12 |
| Cystatin B | 13 |
| A1AG1 | 14 |
| Reg3A | 15 |

* Heavy-isotope labeled amino acid.

TABLE 9

Radiation responsive protein candidates identified and quantified using digested human plasma samples (TBI radiotherapy patients) (shotgun gel-free method).

| Protein name | Dose/Treatment | Day | Up or Down | Max Fold Change Observed |
|---|---|---|---|---|
| AMY1_HUMAN Alpha-amylase 1 (salivary alpha-amylase) | 240-720 cGy/TBI | 1-2 | Up | >10** |
| PRPC_HUMAN Salivary acidic proline-rich phosphoprotein 1/2 precursor (PRP-1/PRP-2) | 240-720 cGy/TBI | 1-2 | Up | >10** |
| PRB2_HUMAN Basic salivary proline-rich protein 2 precursor (Salivary proline-rich protein) | 360-720 cGy/TBI | 1-2 | Up | >10** |

TABLE 9-continued

Radiation responsive protein candidates identified and quantified using digested human plasma samples (TBI radiotherapy patients) (shotgun gel-free method).

| Protein name | Dose/Treatment | Day | Up or Down | Max Fold Change Observed |
|---|---|---|---|---|
| COMP_HUMAN Cartilage oligomeric matrix protein precursor | 360-720 cGy/TBI | 1-2 | Up | ~3** |

**compared to Pre

TABLE 10

Proteins measured by immunoassay in NHP plasma sample sets.

| SRI Study Number | Proteins |
|---|---|
| M918-12 | GCSF, GIP, IL15, IL18, MCP1, A1AGP, ApoC1, CDT, CRP, CST6, ACT, Clusterin, Elastase, Flt3L, Haptoglobin, IDS2, LYVE, Salivary Amylase, TNC, and Transferrin |
| M920-12 | A1AGP, ApoC1, CDT, ACT, Clusterin, Elastase, Flt3L, Haptoglobin, SalivaryAmylase, TNC, TNFa, IL-6, IFNy, IL-18, IL-13, GM-CSF, VEGF, IL-1ra, IL-1b, IL-5, IL-12/23(p40), SCD40L, IL-15, MIP-1b, MIP-1a, TGFa, IL-8, IL-10, MCP-1, IL-17A, IL-4, Il-2, G-CSF |
| A246-12 | ApoC1, CDT, ACT, Clusterin, Elastase, Flt3L, Haptoglobin, SalivaryAmylase, TNC, TNFa, IL-6, IFNy, IL-18, IL-13, GM-CSF, VEGF, IL-1ra, IL-1b, IL-5, IL-12/23(p40), SCD40L, IL-15, MIP-1b, MIP-1a, TGFa, IL-8, IL-10, MCP-1, IL-17A, IL-4, Il-2, G-CSF |

TABLE 11

Replicate values of ACT in control plasma samples for 11 ACT ELISA plates showing interplate CVs.

| Plate | Replicate Values | Average | % Difference |
|---|---|---|---|
| CYT_N_M918_2013_01_30_P1 | 172906.073<br>179355.468 | 176130.771 | 3.66% |
| CYT_N_M918_2013_01_30_P2 | 169251.393<br>154242.947 | 161747.17 | 9.28% |
| CYT_N_M918_2013_01_30_P3 | 159668.12<br>158470.231 | 159069.176 | 0.75% |
| CYT_N_M918_2013_01_30_P4 | 148736.277<br>147457.546 | 148096.912 | 0.86% |
| CYT_N_M918_2013_02_05_P1 | 144767.941<br>151323.591 | 148045.766 | 4.43% |
| CYT_N_M918_2013_02_05_P2 | 140224.426<br>138153.511 | 139188.969 | 1.49% |
| CYT_N_M918_2013_02_05_P3 | 141622.666<br>142416.062 | 142019.364 | 0.56% |
| CYT_N_M918_2013_02_05_P4 | 151292.676<br>155156.751 | 153224.714 | 2.52% |
| CYT_N_M918_2013_03_20_P1 | 163513.535<br>160974.121 | 162243.828 | 1.57% |
| CYT_N_M918_2013_03_20_P2 | 231863.844<br>232378.541 | 232121.193 | 0.22% |
| CYT_N_M918_2013_03_20_P5 | 139811.525<br>141020.278 | 140415.902 | 0.86% |
| | Interplate Average | 160209.433 | |
| | Interplate STD | 26344.9624 | |
| | Interplate CV | 16.44% | |

TABLE 12

Replicate values of Flt3L in control plasma samples for 15 ACT ELISA plates showing interplate CVs.

| Plate | Replicate Values | Average | % Difference |
|---|---|---|---|
| FLT3L_N_M918_2012_09_11_P3 | 0.611<br>0.594 | 0.6025 | 2.82% |
| FLT3L_N_M918_2012_09_11_P3 | 0.699<br>0.599 | 0.649 | 15.41% |
| FLT3L_N_M918_2012_09_11_P4 | 0.635<br>0.658 | 0.6465 | 3.56% |
| FLT3L_N_M918_2012_09_18_P1 | 0.8<br>0.71 | 0.755 | 11.92% |
| FLT3L_N_M918_2012_09_18_P2 | 0.905<br>0.916 | 0.9105 | 1.21% |
| FLT3L_N_M918_2012_09_18_P3 | 0.845<br>0.859 | 0.852 | 1.64% |
| FLT3L_N_M918_2012_09_18_P4 | 0.895<br>0.825 | 0.86 | 8.14% |
| FLT3L_N_M918_2012_12_07_P1 | 0.841<br>0.922 | 0.8815 | 9.19% |
| FLT3L_N_M918_2012_12_07_P2 | 0.83<br>0.865 | 0.8475 | 4.13% |
| FLT3L_N_M918_2012_12_07_P3 | 0.803<br>0.874 | 0.8385 | 8.47% |
| FLT3L_N_M918_2012_12_07_P4 | 0.625<br>0.591 | 0.608 | 5.59% |
| FLT3L_N_M918_2012_12_12_P1 | 0.815<br>0.81 | 0.8125 | 0.62% |
| FLT3L_N_M918_2012_12_12_P2 | 0.791<br>0.756 | 0.7735 | 4.52% |
| FLT3L_N_M918_2012_12_12_P3 | 0.909<br>0.691 | 0.8 | 27.25% |
| FLT3L_N_M918_2012_12_12_P4 | 0.779<br>0.724 | 0.7515 | 7.32% |
| | Interplate Average | 0.773 | |
| | Interplate STD | 0.102 | |
| | Interplate CV | 13.18% | |

TABLE 13

Representative data for a single protein (FLT3L) at a single time point (Day 7). Each dosage group represents 10 animals. For all the proteins (24 total) at all time points (Day 0, 1, 2, 3, and 7), we calculate the mean, standard deviation, minimum value and maximum value in ng/ml for each group. The data below shows a significant increase in mean FLT3L concentration as the dosage increases by day 7.

| Protein | Group | Day 7 | | | |
|---|---|---|---|---|---|
| | | Mean | SD | Min | Max |
| Flt3L | 0 Gy | 0.053111 | 0.020134 | 0.031 | 0.0875 |
| | 1 Gy | 0.0556 | 0.028857 | 0.031 | 0.117 |
| | 2 gy | 0.1713 | 0.101167 | 0.054 | 0.352 |
| | 4 Gy | 0.5481 | 0.10442 | 0.401 | 0.6685 |
| | 8 Gy | 0.8579 | 0.387034 | 0.21 | 1.554 |
| | 10 Gy | 0.60405 | 0.175363 | 0.433 | 0.954 |

TABLE 14

Log base 10 of the p value resulting from a t-test comparing the irradiation group at each day to the control group (0 Gy) at the same day. The comparison by day allows us to eliminate the blood sampling effects for each animal. We calculated the p value for each of the 24 proteins we investigated. The values with log10(pvalues) below −2 represent samples with p values below 0.01.

| | Dose | | | | | | | | | | | | | | |
|---|---|---|---|---|---|---|---|---|---|---|---|---|---|---|---|
| | 1 Gy | | | | | 2 Gy | | | | | 4 Gy | | | | |
| | Day | | | | | | | | | | | | | | |
| | 0 | 1 | 2 | 3 | 7 | 0 | 1 | 2 | 3 | 7 | 0 | 1 | 2 | 3 | 7 |
| GCSF | −0.2 | −0.7 | −0.3 | −0.2 | 0.0 | −0.3 | −0.9 | −0.2 | −0.1 | −0.1 | 0.0 | −0.3 | −0.6 | −0.6 | −1.4 |
| GIP | 0.0 | −0.4 | −0.2 | −0.3 | −0.9 | −0.1 | −0.3 | −0.2 | −0.2 | −0.9 | −1.3 | −0.1 | −0.6 | −0.8 | −1.4 |
| IL15 | −0.8 | −0.6 | −3.8 | −2.0 | −0.9 | −0.2 | −2.6 | −3.2 | −2.5 | −1.8 | −0.6 | −4.5 | −6.9 | −5.3 | −2.8 |
| IL18 | −0.5 | −0.9 | −1.3 | −2.2 | −0.4 | −0.3 | −1.4 | −3.1 | −4.9 | −1.7 | −0.3 | −1.2 | −8.1 | −9.7 | −4.7 |
| MCP1 | −0.4 | −0.2 | −1.5 | −0.5 | −0.6 | −0.9 | −0.3 | −0.9 | −1.0 | −0.8 | −0.3 | −0.1 | −2.1 | −2.4 | −1.5 |
| A1AGP | 0.0 | −0.3 | −0.1 | −0.2 | −0.4 | −0.3 | −0.8 | −1.5 | −1.1 | −0.9 | −0.2 | −0.6 | −0.9 | −1.5 | −0.1 |
| APOC1 | −0.5 | 0.0 | −0.1 | −0.7 | −1.5 | 0.0 | 0.0 | −0.3 | −0.1 | −1.5 | −0.1 | −0.3 | −0.1 | −0.1 | −0.2 |
| CDT | −0.1 | −0.7 | −0.4 | −0.1 | −0.9 | −0.1 | 0.0 | −0.2 | −0.5 | −0.3 | −0.1 | −0.1 | −0.5 | −0.3 | −0.5 |
| CRP | −0.2 | −1.7 | −2.2 | −0.9 | 0.0 | −0.3 | −2.1 | −2.4 | −0.6 | 0.0 | −0.5 | −2.4 | −3.1 | −1.2 | −0.5 |
| CST6 | −0.4 | −0.2 | −0.5 | −0.5 | −0.4 | 0.0 | −0.3 | −0.5 | −0.2 | −0.6 | −0.6 | −0.2 | −0.1 | −0.4 | −0.3 |
| CYT | 0.0 | −0.7 | −2.1 | −1.7 | −0.1 | −0.1 | −2.1 | −3.2 | −1.8 | −0.1 | −0.1 | −4.4 | −6.1 | −4.3 | −1.8 |
| CLU | −0.6 | −0.3 | −1.0 | −0.5 | −0.4 | −0.1 | −0.1 | −0.1 | −0.8 | −0.6 | 0.0 | −0.2 | −0.7 | −0.9 | −0.7 |
| ELANE | −0.6 | 0.0 | 0.0 | −0.5 | −1.0 | −0.6 | −0.3 | 0.0 | −0.2 | −1.1 | −0.2 | −0.1 | −0.2 | −0.1 | −0.8 |
| FLT3L | −0.4 | 0.0 | −0.3 | −1.0 | 0.0 | 0.0 | −0.3 | −1.3 | −3.6 | −3.8 | 0.0 | −2.4 | −6.6 | −8.6 | −12.5 |
| HP | 0.0 | −0.3 | −0.8 | −0.9 | −0.8 | −0.1 | −1.1 | −1.2 | −1.7 | −0.1 | −0.4 | −0.9 | −2.1 | −2.2 | −2.0 |
| IDS2 | −0.4 | 0.0 | −0.7 | −0.1 | −0.4 | −0.2 | −1.4 | −1.3 | −1.5 | −0.4 | 0.0 | −1.6 | −1.6 | −1.3 | −0.3 |
| LYVE | −0.5 | −0.1 | −0.6 | −0.2 | 0.0 | −0.1 | −0.4 | −1.1 | −0.1 | −0.3 | −0.2 | −0.4 | −2.2 | −0.2 | −0.1 |
| SAA | −0.5 | −1.0 | −1.5 | −1.1 | −0.6 | −0.5 | −2.1 | −2.3 | −2.1 | −6.4 | −0.1 | −3.4 | −3.0 | −3.4 | −6.6 |
| TNC | −0.2 | −0.7 | −0.4 | −0.3 | 0.0 | −0.4 | −0.3 | −0.3 | −0.5 | −0.2 | −0.2 | −0.9 | −0.6 | −0.4 | −0.3 |
| TF | −0.4 | −0.6 | −0.2 | −1.0 | −0.6 | −0.2 | 0.0 | −0.1 | 0.0 | −0.2 | −1.4 | −0.4 | −0.3 | 0.0 | −1.5 |
| APOA4 | −0.3 | −0.9 | 0.0 | −0.2 | −1.2 | −0.6 | −0.7 | −1.3 | 0.0 | −3.3 | 0.0 | −0.8 | −1.3 | −0.5 | −3.2 |
| HPX | −0.1 | −0.3 | −0.7 | −1.2 | −0.1 | −0.1 | −1.3 | −1.4 | −2.5 | −0.7 | −0.5 | −1.6 | −2.3 | −4.0 | −1.5 |
| NGAL | −0.4 | 1.5 | 0.0 | −0.6 | −0.1 | −0.4 | −2.2 | −0.8 | −1.9 | −0.1 | −0.8 | −3.4 | −3.9 | −2.7 | −1.2 |
| AMY1A | −0.3 | −1.0 | −0.2 | −0.3 | −0.1 | −0.3 | −2.4 | −0.2 | −0.4 | −0.2 | −0.1 | −4.8 | −0.4 | −1.2 | −1.0 |

| | Dose | | | | | | | | | |
|---|---|---|---|---|---|---|---|---|---|---|
| | 8 Gy | | | | | 10 Gy | | | | |
| | Day | | | | | | | | | |
| | 0 | 1 | 2 | 3 | 7 | 0 | 1 | 2 | 3 | 7 |
| GCSF | −0.1 | −1.1 | −1.3 | −1.0 | −2.5 | 0.0 | −1.0 | −1.2 | −2.4 | −5.1 |
| GIP | −0.4 | −0.2 | −0.6 | −0.5 | −2.2 | −0.8 | −0.9 | −0.3 | −0.3 | −3.6 |
| IL15 | 0.0 | −4.0 | −8.3 | −5.2 | −4.0 | 0.0 | −4.8 | −5.9 | −6.2 | −3.0 |
| IL18 | −0.1 | −2.4 | −9.9 | −9.0 | −4.8 | −0.1 | −2.1 | −6.0 | −11.7 | −3.7 |
| MCP1 | −0.5 | −2.2 | −7.8 | −4.7 | −3.2 | −0.2 | −4.0 | −4.5 | −7.8 | −2.5 |
| A1AGP | −0.6 | −2.2 | −2.4 | −3.8 | −2.8 | 0.0 | −0.8 | −4.0 | −3.0 | −3.2 |
| APOC1 | −0.3 | −0.7 | −0.1 | −0.3 | −1.1 | 0.0 | −0.7 | −1.5 | −0.1 | −0.2 |
| CDT | −0.1 | −1.1 | 0.0 | 0.0 | 0.0 | −0.2 | −2.6 | −1.1 | −0.2 | −0.1 |
| CRP | 0.0 | −3.9 | −3.7 | −1.3 | −1.1 | −0.8 | −3.0 | −3.6 | −2.2 | −1.7 |
| CST6 | −1.0 | −0.2 | −0.3 | −0.5 | −1.7 | −0.1 | −0.3 | −0.3 | 0.0 | −2.0 |
| CYT | −0.3 | −5.8 | −6.5 | −4.5 | −3.1 | 0.0 | −5.7 | −7.7 | −6.3 | −5.1 |

TABLE 14-continued

Log base 10 of the p value resulting from a t-test comparing the irradiation group at each day to the control group (0 Gy) at the same day. The comparison by day allows us to eliminate the blood sampling effects for each animal. We calculated the p value for each of the 24 proteins we investigated. The values with log10(pvalues) below −2 represent samples with p values below 0.01.

| | | | | | | | | | | |
|---|---|---|---|---|---|---|---|---|---|---|
| CLU   | −0.1 | −0.1 | −0.1 | −0.4 | −0.4 | 0.0  | −0.1 | −0.3 | −0.7  | −1.3  |
| ELANE | −0.4 | 0.0  | −0.4 | 0.0  | −3.8 | −0.1 | 0.0  | 0.0  | −0.1  | −1.9  |
| FLT3L | −0.2 | −3.4 | −10.0| −6.9 | −11.0| −0.5 | −2.4 | −9.4 | −11.6 | −12.1 |
| HP    | −0.1 | −0.2 | −2.5 | −3.0 | −5.4 | −1.0 | −0.8 | −3.3 | −3.9  | −7.8  |
| IDS2  | −0.1 | −2.5 | −2.2 | −1.0 | −0.8 | −0.2 | −1.4 | −1.7 | −0.7  | −1.1  |
| LYVE  | −0.5 | −1.4 | 0.0  | 0.0  | 0.0  | −0.1 | 0.0  | −0.1 | 0.0   | 0.0   |
| SAA   | −1.0 | −3.5 | −3.6 | −3.1 | −4.6 | 0.0  | −3.7 | −3.6 | −3.7  | −5.7  |
| TNC   | −0.3 | −1.8 | −1.1 | −0.4 | 0.0  | −0.3 | −0.3 | −0.7 | −1.3  | −1.2  |
| TF    | −1.6 | −0.2 | −0.5 | −0.6 | −2.5 | −0.9 | −0.2 | −1.6 | −1.1  | −1.3  |
| APOA4 | 0.0  | −3.3 | −2.6 | −1.3 | −4.7 | −1.1 | −1.9 | −4.3 | −1.6  | −8.0  |
| HPX   | −0.7 | −2.0 | −3.6 | −4.7 | −2.6 | −0.9 | −1.1 | −3.0 | −4.1  | −4.4  |
| NGAL  | −0.3 | −3.8 | −3.1 | −4.0 | −1.9 | −0.2 | −4.0 | −3.5 | −3.5  | −2.3  |
| AMY1A | −0.2 | −6.8 | −1.6 | −0.2 | −0.2 | −0.6 | −5.6 | −0.9 | −0.1  | 0.0   |

TABLE 15

Accuracy (Acc), false negative rate (FNR), and false positive rate (FPR) for 12 different protein panels based on 5 fold cross validation.

| | Model | | | | | | | | |
|---|---|---|---|---|---|---|---|---|---|
| | Logistic Regress | | | SVM | | | CI Tree | | |
| Protein Panel | Acc | FNR | FPR | Acc | FNR | FPR | Acc | FNR | FPR |
| CYT; Flt3L; IL18; NGAL | 93.2% | 4.9% | 8.0% | 93.9% | 6.1% | 6.1% | 89.2% | 12.3% | 9.8% |
| CYT; Flt3L; HPX; NGAL; APOA4 | 95.2% | 3.7% | 5.5% | 93.9% | 5.1% | 6.8% | 89.4% | 12.3% | 9.5% |
| CYT; Flt3L; NGAL; SAMY | 94.2% | 4.6% | 6.7% | 94.5% | 4.0% | 6.5% | 89.7% | 11.7% | 9.3% |
| CYT; Flt3L; IL15; NGAL; APOA4 | 94.5% | 4.9% | 5.9% | 94.5% | 4.7% | 6.1% | 88.3% | 13.4% | 10.2% |
| CYT; Flt3L; NGAL; APOA4 | 94.1% | 3.8% | 7.3% | 94.8% | 5.0% | 5.3% | 88.7% | 12.2% | 10.7% |
| CYT; Flt3L; NGAL; SAMY; APOA4 | 94.1% | 4.4% | 6.8% | 95.0% | 3.5% | 6.1% | 90.3% | 10.3% | 9.3% |
| CYT; Flt3L; IL18; NGAL; APOA4 | 93.1% | 6.7% | 7.1% | 94.0% | 4.2% | 7.2% | 88.1% | 12.6% | 11.2% |
| CYT; Flt3L; HPX; NGAL | 94.3% | 5.3% | 5.9% | 93.2% | 3.8% | 8.8% | 89.1% | 12.4% | 9.8% |
| CYT; Flt3L; MCP1; NGAL; APOA4 | 93.6% | 4.2% | 7.9% | 94.2% | 7.7% | 4.6% | 88.6% | 13.6% | 9.6% |
| CYT; Flt3L; IL15; NGAL | 94.5% | 4.6% | 6.1% | 93.9% | 5.3% | 6.6% | 88.9% | 13.7% | 9.4% |
| CYT; Flt3L; NGAL | 94.8% | 4.1% | 6.0% | 93.2% | 3.6% | 8.9% | 88.7% | 12.2% | 10.7% |
| CYT; Flt3L; MCP1; NGAL | 95.2% | 4.4% | 5.0% | 94.1% | 7.1% | 5.1% | 88.3% | 14.2% | 9.7% |

TABLE 16

Average and standard deviation for 7 iterations of 5 fold cross validation using a panel of 4 proteins (ACT, FLT3L, AMY1A, and IL15). We used a 30% probability of exposures as the cutoff to classify a sample as high dose (≥4 Gy) exposure. Overall the model performed well and the low standard deviation between different random splits of the data improves confidence in the results.

| Attribute | Mean | Standard Deviation |
|---|---|---|
| Accuracy | 96.5% | 0.3% |
| Sensitivity | 98.1% | 0.6% |
| Specificity | 95.5% | 0.4% |
| PPV | 93.5% | 0.5% |
| NPV | 98.7% | 0.4% |
| FPR | 4.5% | 0.4% |
| FNR | 1.9% | 0.6% |

TABLE 17

Four samples with average probability of exposure less than 50% from 7 iterations of 5 fold cross validation using AT, FLT3L, IL15, and AMY1A.

| Sample | Dose (Gy) | Day | Probability Exposed | # Iterations False Negative |
|---|---|---|---|---|
| F5505B | 8 | 3 | 0.29% | 7 |
| F4501C | 4 | 1 | 20.6% | 7 |
| M4005B | 4 | 1 | 33.5% | 7 |
| F4503C | 4 | 2 | 44.3% | 4 |

TABLE 18

Four samples with average probability of no exposure less than 50% from 7 iterations of 5 fold cross validation using AT, FLT3L, IL15, and AMY1A.

| Sample | Dose (Gy) | Day | Probability Not Exposed | # Iterations False Positive |
|---|---|---|---|---|
| F3505B | 2 | 3 | 0.03% | 7 |
| M3005B | 2 | 2 | 3.2% | 7 |
| M3005B | 2 | 3 | 7.2% | 7 |
| F3501C | 2 | 3 | 46.1% | 7 |
| F3501C | 2 | 1 | 47.6% | 7 |
| M3001A | 2 | 2 | 48.2% | 7 |

TABLE 19

Coefficient of variation (CV) results from the LFA repeatability assay for two target biomarkers, Salivary Alpha Amylase (AMY1A) and Fms-related tyrosine kinase 3 ligand (FLT3L). We performed the same LFA assay for each analyte at four different concentrations in triplicate on three different days. The CVs listed in the table below represent those 3 replicates on each day and the interday for the average on standard deviation for the 3 different days.

| Protein & Conc | Day 1 | Day 2 | Day 3 | Inter-Day |
|---|---|---|---|---|
| AMY1A (5 ng/mL) | 6.6% | 4.3% | 3.2% | 4.9% |
| AMY1A (25 ng/mL) | 6.1% | 8.5% | 10.4% | 9.9% |
| AMY1A (50 ng/mL) | 8.5% | 5.8% | 12.4% | 9.5% |
| AMY1A (100 ng/mL) | 12.4% | 8.1% | 9.2% | 11.6% |
| FLT3L (0.002 ng/mL) | 2.7% | 0.7% | 9.1% | 5.1% |
| FLT3L (0.1 ng/mL) | 2.5% | 1.8% | 2.0% | 5.1% |
| FLT3L (0.5 ng/mL) | 4.6% | 2.9% | 2.3% | 7.5% |
| FLT3L (1 ng/mL) | 5.9% | 7.0% | 0.2% | 6.8% |

TABLE 20

Average signal to background ratio (SBR) and standard deviations for 15 measurements of the same wicks for 2 analytes (FLT3L and AMY1A) at 2 different concentrations.

| Protein & Concentration | Average SBR | Standard Deviation SBR | Coefficient of Variation (%) |
|---|---|---|---|
| AMY1A (5 ng/ml) | 1.33 | 0.011 | 0.84% |
| AMY1A (50 ng/ml) | 6.11 | 0.098 | 1.60% |
| FLT3L (0.1 ng/ml) | 1.15 | 0.018 | 1.60% |
| FLT3L (1 ng/ml) | 1.39 | 0.039 | 2.79% |

TABLE 21

Results from 10 RBC filter cartridge runs under the same conditions compared to the control that was spun down whole blood. We chose 1 PSI and 175 ul of input volume. We measure cellularity and lysis using 412 nm absorption. The FLT3L was spiked into the sample at 210 ng/ml and read out using an ELISA. The results show that at 1PSI we have significantly less cells remaining, lysis is as good or better than centrifugation, and we were within 10% (the ELISA assay CV) of the target 210 ng/ml concentration.

| Tube | Pressure (PSI) | Input Vol (μl) | Recovered Vol (μl) | Cellularity (412 nm) | Lysis (412 nm) | FLT3L Conc (pg/ml) |
|---|---|---|---|---|---|---|
| Ctrl | N/A | N/A | N/A | 0.35 | 0.35 | 176 |
| 1 | 1 | 175 | 74 | 0.00 | 0.31 | 234 |
| 2 | 1 | 175 | 50 | 0.02 | 0.35 | 223 |
| 3 | 1 | 175 | 108 | 0.01 | 0.32 | 205 |
| 4 | 1 | 175 | 61 | 0.01 | 0.31 | 219 |
| 5 | 1 | 175 | 133 | 0.01 | 0.28 | 207 |
| 6 | 1 | 175 | 64 | 0.02 | 0.40 | 232 |
| 7 | 1 | 175 | 47 | 0.02 | 0.36 | 222 |
| 8 | 1 | 175 | 45 | 0.00 | 0.31 | 197 |
| 9 | 1 | 175 | 135 | 0.03 | 0.32 | 224 |
| 10 | 1 | 175 | 113 | 0.01 | 0.39 | 222 |

What is claimed is:

1. A method of treating a person for radiation exposure, wherein the person has been exposed to radiation, the method comprising the steps of:

a. obtaining or having obtained a sample from the person;

b. detecting the presence and level of biomarkers for ionizing radiation in the sample, wherein the biomarkers comprise (i) alpha-1-Antichymotrypsin (ACT), (ii) Fms-related tyrosine kinase 3 ligand (Flt3L), (iii) Salivary alpha amylase (AMY1A) and (iv) IL-15;

c. determining a change in the level of the biomarkers in the sample compared with the level of the biomarkers from a corresponding non-irradiated control reference indicating the person has been exposed to radiation; and d. administering an effective amount of an ionizing radiation treatment to the person.

2. The method of claim 1, further comprising separating biomarkers of a blood sample of the person prior to step (i).

3. The method of claim 1, wherein the detecting step comprises a lateral flow immunoassay, ELISA, microsphere-based immunoassay, Western blot, immune-dot blot, or quantitative mass spectroscopy.

4. The method of claim 1, wherein the radiation exposure is >2Gy.

5. The method of claim 1, wherein the detecting step occurs 1-14 days after the radiation exposure.

6. A method of diagnosing and treating a person for radiation exposure, wherein the person has been exposed to radiation at an amount greater than or equal to 2Gy, the method comprising the steps of:

a. detecting the presence and level of biomarkers for ionizing radiation are present in a sample obtained from a subject, wherein the biomarkers comprise (i) alpha-1-Antichymotrypsin (ACT), (ii) Fms-related tyrosine kinase 3 ligand (Flt3L), (iii) Salivary alpha amylase (AMY1A), and (iv) IL-15;

b. diagnosing the person as being irradiation exposed to greater than or equal to 2Gy
  i. when a change in the amounts of the biomarkers, compared with corresponding non-irradiated control reference amounts of the biomarkers is detected; and c. administering an effective amount of an ionizing radiation treatment to the person.

7. The method of claim 6, further comprising separating biomarkers of a blood sample of the person prior to step (i).

8. The method of claim 6, wherein the detecting step comprises a lateral flow immunoassay, ELISA, microsphere-based immunoassay, Western blot, immune-dot blot, or quantitative mass spectroscopy.

9. The method of claim 6, wherein the detecting step occurs 1-14 days after the radiation exposure.

10. The method of claim 1, wherein the change in level of the biomarkers in the sample is at least about a 2 fold increase over the non-irradiated control reference.

11. The method of claim 6, wherein the change in level of the biomarkers in the sample is at least about a 2 fold increase over the non-irradiated control reference.

* * * * *